(12) United States Patent
Fotouhi et al.

(10) Patent No.: US 7,705,007 B2
(45) Date of Patent: Apr. 27, 2010

(54) CIS-IMIDAZOLINES

(75) Inventors: Nader Fotouhi, Basking Ridge, NJ (US); Gregory Jay Haley, San Diego, CA (US); Klaus B. Simonsen, Frederiksberg (DK); Binh Thanh Vu, North Caldwell, NJ (US); Stephen Evan Webber, San Diego, CA (US)

(73) Assignee: Hoffmann-La Roche Inc., Nutley, NJ (US)

( * ) Notice: Subject to any disclaimer, the term of this patent is extended or adjusted under 35 U.S.C. 154(b) by 471 days.

(21) Appl. No.: 11/654,102

(22) Filed: Jan. 17, 2007

(65) Prior Publication Data

US 2007/0167437 A1  Jul. 19, 2007

Related U.S. Application Data

(60) Provisional application No. 60/759,770, filed on Jan. 18, 2006.

(51) Int. Cl.
| | |
|---|---|
| *A61K 31/5377* | (2006.01) |
| *A61K 31/506* | (2006.01) |
| *A61K 31/4545* | (2006.01) |
| *A61K 31/496* | (2006.01) |
| *C07D 413/14* | (2006.01) |
| *C07D 403/14* | (2006.01) |
| *C07D 401/14* | (2006.01) |
| *C07D 241/02* | (2006.01) |

(52) U.S. Cl. ............. 514/269; 514/254.05; 514/252.19; 514/235.8; 544/370; 544/364; 544/357; 544/295; 544/121

(58) Field of Classification Search ................. 544/121, 544/295, 357, 364, 370; 514/235.8, 252.19, 514/254.05, 269
See application file for complete search history.

(56) References Cited

U.S. PATENT DOCUMENTS

| 6,617,346 B1 | 9/2003 | Kong et al. |
| 6,734,302 B2 * | 5/2004 | Kong et al. ................. 544/139 |
| 2004/0259867 A1 | 12/2004 | Fotouhi et al. |
| 2005/0282803 A1 * | 12/2005 | Haley et al. ............... 514/227.5 |

FOREIGN PATENT DOCUMENTS

| EP | 363061 | 7/1992 |
| WO | WO00/78725 | 12/2000 |
| WO | WO 03/051359 A1 | 6/2003 |
| WO | WO 2005/110996 A1 | 11/2005 |
| WO | WO 2005/123691 A1 | 12/2005 |

OTHER PUBLICATIONS

Wells, et. al., J. Org. Chem (1972) 37, 2158-2161.
Hunter, et. al., Can J. Chem (1972), vol. 50 p. 669-77.
McCapra, et. al., Photochen and Photobiol (1965), 4, 1111-1121.
Zupanc, et. al., Bull. Soc. Chem & Tech (Yugoslavia) 1980-81, 27/28,71-80.
Vassilev, L.T., et al., Science, American Association for the Advancement of Science, vol. 303, No. 5659, pp. 844-848 (2004), XP002338500.
David, C., Fry, et al., Journal of Biomolecular NMR, vol. 30, No. 2, pp. 163-173 (2004), XP019249439.

* cited by examiner

*Primary Examiner*—Rebecca L Anderson
*Assistant Examiner*—Jason M Nolan
(74) *Attorney, Agent, or Firm*—George W. Johnston; Patricia S. Rocha-Tramaloni

(57) ABSTRACT

There are provided compounds of the formula I

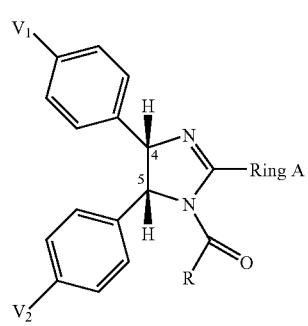

wherein R, $V_1$, $V_2$ and Ring A are described herein. The compounds exhibit anticancer activity.

11 Claims, No Drawings

US 7,705,007 B2

CIS-IMIDAZOLINES

PRIORITY TO RELATED APPLICATIONS

This application claims the benefit of U.S. Provisional Application No. 60/759,770, filed Jan. 18, 2006, which is hereby incorporated by reference in its entirety.

FIELD OF THE INVENTION

This invention is related to at least one compound selected from a compound of formula I

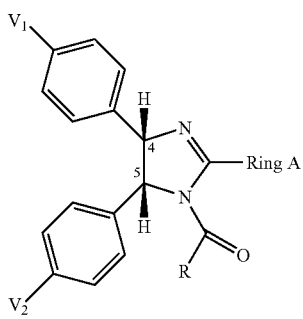

or the pharmaceutically acceptable salts thereof, wherein $V_1$, $V_2$, R and ring A are described in this application. These compounds are believed to inhibit the interaction of MDM2 protein with a p53-like peptide and have antiproliferative activity.

BACKGROUND OF THE INVENTION p53 is a tumor suppresser protein that plays a central role in protection against development of cancer. It guards cellular integrity and prevents the propagation of permanently damaged clones of cells by the induction of growth arrest or apoptosis. At the molecular level, p53 is a transcription factor that can activate a panel of genes implicated in the regulation of cell cycle and apoptosis. p53 is a potent cell cycle inhibitor which is tightly regulated by MDM2 at the cellular level. MDM2 and p53 form a feedback control loop. MDM2 can bind p53 and inhibit its ability to transactivate p53-regulated genes. In addition, MDM2 mediates the ubiquitin-dependent degradation of p53. p53 can activate the expression of the MDM2 gene, thus raising the cellular level of MDM2 protein. This feedback control loop insures that both MDM2 and p53 are kept at a low level in normal proliferating cells. MDM2 is also a cofactor for E2F, which plays a central role in cell cycle regulation.

The ratio of MDM2 to p53 (E2F) is dysregulated in many cancers. Frequently occurring molecular defects in the p16INK4/p19ARF locus, for instance, have been shown to affect MDM2 protein degradation. Inhibition of MDM2-p53 interaction in tumor cells with wild-type p53 should lead to accumulation of p53, cell cycle arrest and/or apoptosis. MDM2 antagonists, therefore, can offer a novel approach to cancer therapy as single agents or in combination with a broad spectrum of other antitumor therapies. The feasibility of this strategy has been shown by the use of different macromolecular tools for inhibition of MDM2-p53 interaction (e.g. antibodies, antisense oligonucleotides, peptides). MDM2 also binds E2F through a conserved binding region as p53 and activates E2F-dependent transcription of cyclin A, suggesting that MDM2 antagonists might have effects in p53 mutant cells.

Wells et al. *J. Org. Chem.,* 1972, 37, 2158-2161, report synthesis of imidazolines. Hunter et al., *Can. J. Chem.,* 1972, Vol. 50, pgs. 669-77, report the preparation of amarine and isoamarine compounds which had previously been studied for chemiluminescence (McCapra et al. *Photochem. and Photobiol.* 1965, 4, 1111-1121). Zupanc et al. *Bull. Soc. Chem. & Tech.* (Yugoslavia) 1980-81, 27/28, 71-80, report the use of triaryl imidazolines as starting materials in the preparation of EDTA derivatives.

EP 363 061 to Matsumoto reports imidazoline derivatives useful as immunomodulators. The compounds were indicated to have low toxicity. Treatment and/or prevention of rheumatoid arthritis, multiple sclerosis, systemic lupus, erythemathodes, and rheumatic fever were implicated. WO 00/78725 to Choueiry et al. report a method for making substituted amidine compounds, and indicate that imidazoline-type compounds may be useful in the treatment of diabetes or related diseases involving impaired glucose disposal.

U.S. Pat. No. 6,617,346 B1 (issued Sep. 9, 2003), U.S. Pat. No. 6,734,302 B2 (issued May 11, 2004), US20040259884 A1 (published Dec. 23, 2004), US20040259867 A1 (published Dec. 23, 2004) disclose related cis-imidazolines.

DETAILED DESCRIPTION OF THE INVENTION

The present invention provides cis-imidazolines which are small molecule inhibitors of the MDM2-p53 interaction. In cell-free and cell-based assays, compounds of the present invention are shown to inhibit the interaction of MDM2 protein with a p53-like peptide. Therefore, the activity of MDM2 antagonists is likely linked to its mechanism of action. These compounds can be potent and selective anticancer agents.

The present invention provides at least one compound of formula I

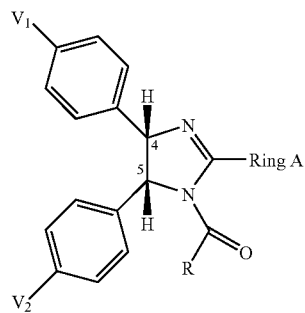

and the pharmaceutically acceptable salts and esters thereof, wherein

Ring A is:

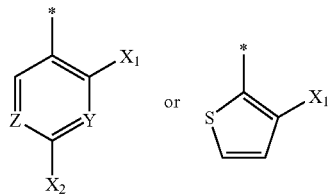

$X_1$ is selected from the group consisting of
  lower alkoxy, and
  lower alkoxy substituted by trifluoromethyl or fluorine;

$X_2$ is selected from the group consisting of
  hydrogen,
  thioalkyl,
  lower alkyl,
  lower alkoxy,
  morpholino, and
  —$NX_3X_4$;

$X_3$ and $X_4$ are independently selected from the group consisting of
  hydrogen,
  lower alkyl,
  lower alkyl substituted by lower alkoxy or cyano, and
  lower alkoxy;

Y and Z are independently selected from the group consisting of:
  carbon, and
  nitrogen;

$V_1$ and $V_2$ are independently selected from the group consisting of
  halogen,
  cyano, and
  acetylene;

R is selected from the group consisting of
  piperidinyl substituted by five or six membered heterocycle,
  piperidinyl substituted by —$NX_3X_4$, and

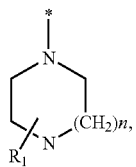

wherein
  n=1 or 2, $R_1$ can be one or more substituents selected from the group consisting of
  hydrogen,
  oxo,
  lower alkyl substituted by $R_2$,
  —C(O)$R_3$, and
  —$SO_2$-lower alkyl;

$R_2$ is selected from the group consisting of
  hydroxy,
  lower alkoxy,
  trifluoromethyl,
  -cyano,
  —NH—$SO_2$-lower alkyl,
  —NH—C(O)-lower alkyl,
  —C(O)-lower alkyl,
  —C(O)$R_4$,
  —C(O)—$NX_3X_4$,
  —$SO_2$-lower alkyl,
  —$SO_2$—$NX_3X_4$, $R_3$ is selected from the group consisting of
  five membered heterocycle,
  lower alkyl,
  lower alkoxy, and
  lower alkyl substituted by lower alkoxy; and $R_4$ is selected from the group consisting of
  hydroxy,
  lower alkoxy,
  morpholino, and
  —$NX_3X_4$.

Preferred compounds are compounds of formula I wherein $V_1$ and $V_2$ are each independently selected from —Cl and —Br.

Further preferred compounds are compounds of formula I wherein R is piperazinyl substituted by oxo or lower alkyl substituted by $R_2$.

Also preferred compounds are compounds in which the two hydrogen atoms of the imidazoline ring are in a cis configuration to each other. The compounds may be in a racemic form and may be optically active. The preferred absolute stereochemistry at the 4 and 5 position of the imidazoline ring are S and R, respectively.

Especially preferred compounds are for example:
cis-4-[(4,5-Bis-(4-chloro-phenyl)-2-(2-ethoxy-pyridin-3-yl)-4,5-dihydro-imidazole-1-carbonyl]-piperazin-2-one,
cis-2-{4-[4,5-Bis-(4-chloro-phenyl)-2-(2-ethoxy-pyridin-3-yl)-4,5-dihydro-imidazole-1-carbonyl]-piperazin-1-yl}-N,N-dimethyl-acetamide,
cis-[4,5-Bis-(4-chloro-phenyl)-2-(2-ethoxy-pyridin-3-yl)-4,5-dihydro-imidazol-1-yl]-[4-(2-methanesulfonyl-ethyl)-piperazin-1-yl]-methanone,
cis-2-{4-[4,5-Bis-(4-chloro-phenyl)-2-(2-ethoxy-pyridin-3-yl)-4,5-dihydro-imidazole-1-carbonyl]-piperazin-1-yl}-1-morpholin-4-yl-ethanone,
cis-4-[4,5-Bis-(4-chloro-phenyl)-2-(4-ethoxy-2-trifluoromethyl-pyrimidin-5-yl)-4,5-dihydro-imidazole-1-carbonyl]-piperazin-2-one,
cis-[4,5-Bis-(4-chloro-phenyl)-2-(4-ethoxy-2-trifluoromethyl-pyrimidin-5-yl)-4,5-dihydro-imidazol-1-yl]-[4-(2-methanesulfonyl-ethyl)-piperazin-1-yl]-methanone,
cis-2-{4-[4,5-Bis-(4-chloro-phenyl)-2-(4-ethoxy-2-trifluoromethyl-pyrimidin-5-yl)-4,5-dihydro-imidazole-1-carbonyl]-piperazin-1-yl}-1-morpholin-4-yl-ethanone,
cis-4-[4,5-Bis-(4-chloro-phenyl)-2-(2,4-diethoxy-pyrimidin-5-yl)-4,5-dihydro-imidazole-1-carbonyl]-piperazin-2-one,
cis-2-{4-[4,5-Bis-(4-chloro-phenyl)-2-(2,4-diethoxy-pyrimidin-5-yl)-4,5-dihydro-imidazole-1-carbonyl]-piperazin-1-yl}-N,N-dimethyl-acetamide,
cis-[4,5-Bis-(4-chloro-phenyl)-2-(2,4-diethoxy-pyrimidin-5-yl)-4,5-dihydro-imidazol-1-yl]-[4-(2-methanesulfonyl-ethyl)-piperazin-1-yl]-methanone,
cis-2-{4-[4,5-Bis-(4-chloro-phenyl)-2-(2,4-diethoxy-pyrimidin-5-yl)-4,5-dihydro-imidazole-1-carbonyl]-piperazin-1-yl}-1-morpholin-4-yl-ethanone,
cis-4-[4,5-Bis-(4-chloro-phenyl)-2-(4-ethoxy-2-methylsulfanyl-pyrimidin-5-yl)-4,5-dihydro-imidazole-1-carbonyl]-piperazin-2-one,
cis-2-{4-[4,5-Bis-(4-chloro-phenyl)-2-(4-ethoxy-2-methylsulfanyl-pyrimidin-5-yl)-4,5-dihydro-imidazole-1-carbonyl]-piperazin-1-yl}-N,N-dimethyl-acetamide,
cis-[4,5-Bis-(4-chloro-phenyl)-2-(4-ethoxy-2-methylsulfanyl-pyrimidin-5-yl)-4,5-dihydro-imidazol-1-yl]-[4-(2-methanesulfonyl-ethyl)-piperazin-1-yl]-methanone, cis-2-{4-[4,5-Bis-(4-chloro-phenyl)-2-(4-ethoxy-2-methyl-sulfanyl-pyrimidin-5-yl)-4,5-dihydro-imidazole-1-carbonyl]-piperazin-1-yl}-1-morpholin-4-yl-ethanone, cis-4-[4,5-Bis-(4-chloro-phenyl)-2-(4-ethoxy-2-methyl-pyrimidin-5-yl)-4,5-dihydro-imidazole-1-carbonyl]-piperazin-2-one, cis-2-{4-[4,5-Bis-(4-chloro-phenyl)-2-(4-ethoxy-2-methyl-pyrimidin-5-yl)-4,5-dihydro-imidazole-1-carbonyl]-piperazin-1-yl}-N,N-dimethyl-acetamide, cis-[4,5-Bis-(4-chloro-phenyl)-2-(4-ethoxy-2-methyl-pyrimidin-5-yl)-4,5-dihydro-imidazol-1-yl]-[4-(2-methanesulfonyl-ethyl)-piperazin-1-yl]-methanone, cis-2-{4-[4,5-Bis-(4-chloro-phenyl)-2-(4-ethoxy-2-methyl-pyrimidin-5-yl)-4,5-dihydro-imidazole-1-carbonyl]-piperazin-1-yl}-1-morpholin-4-yl-ethanone, cis-4-[2-(2-tert-Butyl-4-ethoxy-pyrimidin-5-yl)-4,5-bis-(4-chloro-phenyl)-4,5-dihydro-imidazole-1-carbonyl]-piperazin-2-one hydrochloride, cis-2-{4-[2-(2-tert-Butyl-4-ethoxy-pyrimidin-5-yl)-4,5-bis-(4-chloro-phenyl)-4,5-dihydro-imidazole-1-carbonyl]-piperazin-1-yl}-N,N-dimethyl-acetamide hydrochloride, cis-[2-(2-tert-Butyl-4-ethoxy-pyrimidin-5-yl)-4,5-bis-(4-chloro-phenyl)-4,5-dihydro-imidazol-1-yl]-[4-(2-methanesulfonyl-ethyl)-piperazin-1-yl]-methanone hydrochloride, cis-2-{4-[2-(2-tert-Butyl-4-ethoxy-pyrimidin-5-yl)-4,5-bis-(4-chloro-phenyl)-4,5-dihydro-imidazole-1-carbonyl]-piperazin-1-yl}-1-morpholin-4-yl-ethanone, cis-[2-(2-tert-Butyl-4-ethoxy-pyrimidin-5-yl)-4,5-bis-(4-chloro-phenyl)-4,5-dihydro-imidazol-1-yl]-(4-dimethylamino-piperidin-1-yl)-methanone, cis-[2-(2-tert-Butyl-4-ethoxy-pyrimidin-5-yl)-4,5-bis-(4-chloro-phenyl)-4,5-dihydro-imidazol-1-yl]-(4-pyrrolidin-1-yl-piperidin-1-yl)-methanone, cis-1-{4-[2-(2-tert-Butyl-4-ethoxy-pyrimidin-5-yl)-4,5-bis-(4-chloro-phenyl)-4,5-dihydro-imidazole-1-carbonyl]-piperazin-1-yl}-ethanone, cis-[2-(2-tert-Butyl-4-ethoxy-pyrimidin-5-yl)-4,5-bis-(4-chloro-phenyl)-4,5-dihydro-imidazol-1-yl]-(4-methyl-piperazin-1-yl)-methanone, cis-[2-(2-tert-Butyl-4-ethoxy-pyrimidin-5-yl)-4,5-bis-(4-chloro-phenyl)-4,5-dihydro-imidazol-1-yl]-[4-(3-methanesulfonyl-propyl)-piperazin-1-yl]-methanone, cis-[2-(2-tert-Butyl-4-ethoxy-pyrimidin-5-yl)-4,5-bis-(4-chloro-phenyl)-4,5-dihydro-imidazol-1-yl]-[4-(2-hydroxy-ethyl)-piperazin-1-yl]-methanone, 2-{4-[(4S,5R)-2-(2-tert-Butyl-4-ethoxy-pyrimidin-5-yl)-4,5-bis-(4-chloro-phenyl)-4,5-dihydro-imidazole-1-carbonyl]-piperazin-1-yl}-1-morpholin-4-yl-ethanone, 4-[(4S,5R)-2-(2-tert-Butyl-4-ethoxy-pyrimidin-5-yl)-4,5-bis-(4-chloro-phenyl)-4,5-dihydro-imidazole-1-carbonyl]-piperazin-2-one, cis-4-[4,5-Bis-(4-chloro-phenyl)-2-(4,6-diethoxy-pyridin-3-yl)-4,5-dihydro-imidazole-1-carbonyl]-piperazin-2-one hydrochloride, cis-[4,5-Bis-(4-chloro-phenyl)-2-(4,6-diethoxy-pyridin-3-yl)-4,5-dihydro-imidazol-1-yl]-[4-(2-hydroxy-ethyl)-piperazin-1-yl]-methanone hydrochloride, 2-{4-[(4S,5R)-4,5-Bis-(4-chloro-phenyl)-2-(3-ethoxy-thiophen-2-yl)-4,5-dihydro-imidazole-1-carbonyl]-piperazin-1-yl}-N-tert-butyl-acetamide, 2-{4-[(4S,5R)-4,5-Bis-(4-chloro-phenyl)-2-(3-ethoxy-thiophen-2-yl)-4,5-dihydro-imidazole-1-carbonyl]-piperazin-1-yl}-acetamide, 2-{4-[(4S,5R)-4,5-Bis-(4-chloro-phenyl)-2-(3-ethoxy-thiophen-2-yl)-4,5-dihydro-imidazole-1-carbonyl]-piperazin-1-yl}-N,N-bis-(2-methoxy-ethyl)-acetamide, 2-{4-[(4S,5R)-4,5-Bis-(4-chloro-phenyl)-2-(3-ethoxy-thiophen-2-yl)-4,5-dihydro-imidazole-1-carbonyl]-piperazin-1-yl}-N-methoxy-N-methyl-acetamide, 2-{4-[(4S,5R)-4,5-Bis-(4-chloro-phenyl)-2-(3-ethoxy-thiophen-2-yl)-4,5-dihydro-imidazole-1-carbonyl]-piperazin-1-yl}-N-isopropyl-N-methyl-acetamide, 2-{4-[(4S,5R)-4,5-Bis-(4-chloro-phenyl)-2-(3-ethoxy-thiophen-2-yl)-4,5-dihydro-imidazole-1-carbonyl]-piperazin-1-yl}-N-(2-cyano-ethyl)-N-methyl-acetamide, cis-2-{4-[4,5-Bis-(4-chloro-phenyl)-2-(3-ethoxy-thiophen-2-yl)-4,5-dihydro-imidazole-1-carbonyl]-piperazin-1-yl}-N-(2-methoxy-1-methyl-ethyl)-acetamide,

[(4S,5R)-4,5-Bis-(4-chloro-phenyl)-2-(3-ethoxy-thiophen-2-yl)-4,5-dihydro-imidazol-1-yl]-[4-(3,5-dimethyl-isoxazole-4-carbonyl)-piperazin-1-yl]-methanone,

[(4S,5R)-4,5-Bis-(4-chloro-phenyl)-2-(3-ethoxy-thiophen-2-yl)-4,5-dihydro-imidazol-1-yl]-(4-ethanesulfonyl-piperazin-1-yl)-methanone, N-(2-{4-[(4S,5R)-4,5-Bis-(4-chloro-phenyl)-2-(3-ethoxy-thiophen-2-yl)-4,5-dihydro-imidazole-1-carbonyl]-piperazin-1-yl}ethyl)-methanesulfonamide,

[(4S,5R)-4,5-Bis-(4-chloro-phenyl)-2-(3-ethoxy-thiophen-2-yl)-4,5-dihydro-imidazol-1-yl]-[4-(3-methanesulfonyl-propyl)-piperazin-1-yl]-methanone,

[(4S,5R)-4,5-Bis-(4-chloro-phenyl)-2-(3-ethoxy-thiophen-2-yl)-4,5-dihydro-imidazol-1-yl]-[4-(2-methanesulfonyl-ethyl)-piperazin-1-yl]-methanone and 2-{4-[(4S,5R)-4,5-Bis-(4-chloro-phenyl)-2-(3-ethoxy-thiophen-2-yl)-4,5-dihydro-imidazole-1-carbonyl]-piperazin-1-yl}-1-morpholin-4-yl-ethanone.

"Effective amount" means an amount that is effective to prevent, alleviate or ameliorate symptoms of disease or prolong the survival of the subject being treated.

"Halogen" means fluorine, chlorine, bromine or iodine.

"Hetero atom" means an atom selected from N, O and S.

"$IC_{50}$" refers to the concentration of a particular compound required to inhibit 50% of a specific measured activity. $IC_{50}$ can be measured, inter alia, as is described subsequently.

"Alkyl" denotes a straight-chained or branched saturated aliphatic hydrocarbon.

"Cycloalkyl" means a non-aromatic, partially or completely saturated monovalent cyclic hydrocarbon radical containing 3 to 8 atoms. Preferred examples of cycloalkyl groups are cyclopropyl, cyclobutyl, and cyclopentyl.

"Lower alkyl" groups denote C1-C6 alkyl groups and include methyl, ethyl, propyl, isopropyl, butyl, t-butyl, 2-butyl, pentyl, hexyl, and the like. Generally, lower alkyl is preferably C1-C4 alkyl, and more preferably C1-C3 alkyl.

"Alkoxy" denotes —O-alkyl. "Lower alkoxy" denotes —O-lower alkyl.

"Pharmaceutically acceptable ester" refers to a conventionally esterified compound of formula I having a carboxyl group, which esters retain the biological effectiveness and properties of the compounds of formula I and are cleaved in vivo (in the organism) to the corresponding active carboxylic acid.

Information concerning esters and the use of esters for the delivery of pharmaceutical compounds is available in Design of Prodrugs, Bundgaard H ed. (Elsevier, 1985). See also, H. Ansel et al., Pharmaceutical Dosage Forms and Drug Delivery Systems (6th Ed. 1995) at pp. 108-109; Krogsgaard-Larsen, et al., Textbook of Drug Design and Development (2d Ed. 1996) at pp. 152-191.

"Pharmaceutically acceptable salt" refers to conventional acid-addition salts or base-addition salts that retain the biological effectiveness and properties of the compounds of the present invention and are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Sample base-addition salts include those derived from ammonium, potassium, sodium and, quaternary ammonium hydroxides, such as for example, tetramethylammonium hydroxide. Chemical modification of a pharmaceutical compound (i.e. drug) into a salt is a technique well known to pharmaceutical chemists to obtain improved physical and chemical stability, hygroscopicity, flowability and solubility of compounds. See, e.g., H. Ansel et al., Pharmaceutical Dosage Forms and Drug Delivery Systems (6th Ed. 1995) at pp. 196 and 1456-1457.

"Pharmaceutically acceptable," such as pharmaceutically acceptable carrier, excipient, etc., means pharmacologically acceptable and substantially non-toxic to the subject to which the particular compound is administered.

"Substituted" means that the substitution can occur at one or more positions and, unless otherwise indicated, that the substituents at each substitution site are independently selected from the specified options.

"Therapeutically effective amount" means an amount of at least one designated compound, that significantly inhibits proliferation and/or prevents differentiation of a human tumor cell, including human tumor cell lines.

Compounds of the present invention as exemplified advantageously show IC50s from about 0.030 uM to about 7 uM.

The compounds of the present invention are useful in the treatment or control of cell proliferative disorders, in particular oncological disorders. These compounds and formulations containing said compounds may be useful in the treatment or control of solid tumors, such as, for example, breast, colon, lung and prostate tumors.

A therapeutically effective amount of a compound in accordance with this invention means an amount of compound that is effective to prevent, alleviate or ameliorate symptoms of disease or prolong the survival of the subject being treated. Determination of a therapeutically effective amount is within the skill in the art.

The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 10 mg to about 10,000 mg, preferably from about 200 mg to about 1,000 mg, should be appropriate, although the upper limit may be exceeded when indicated. The daily dosage can be administered as a single dose or in divided doses, or for parenteral administration, it may be given as continuous infusion.

The present invention also provides pharmaceutical compositions comprising at least one compound of formula I, or a pharmaceutically acceptable salt or ester thereof, and a pharmaceutically acceptable carrier or excipient.

The compounds of the present invention can be prepared according to the following scheme 1.

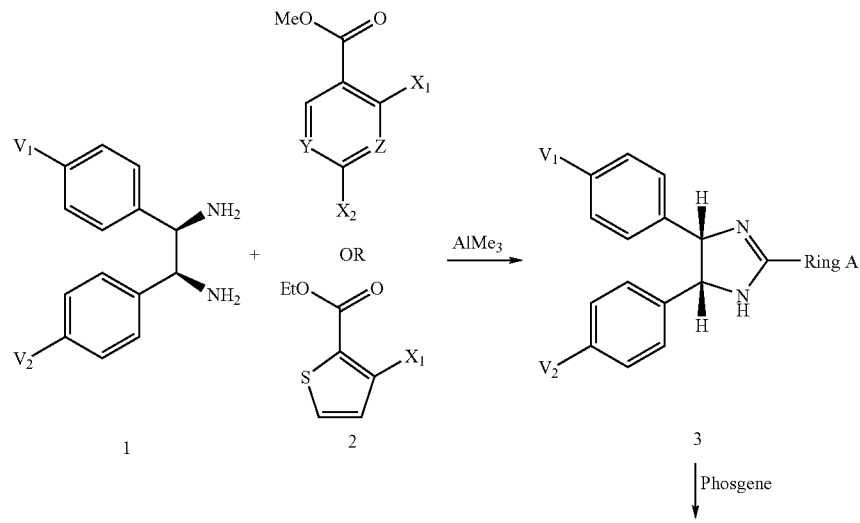

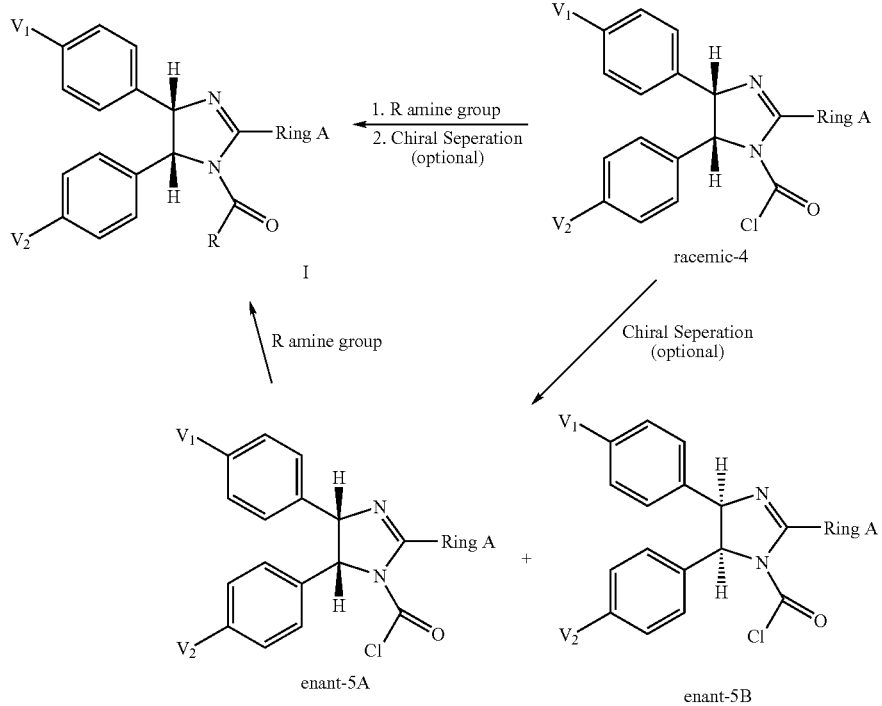

The synthesis commences with the coupling reaction of the ester 2 with meso-1,2-bis-(4-chlorophenyl)-ethane-1,2-diamine 1 (prepared according to the procedure described by Jennerwein, M. et al. *Cancer Res. Clin. Oncol.* 1988, 114, 347-58; Vogtle, F.; Goldschmitt, E. *Chem. Ber.* 1976, 109, 1-40) using trimethylaluminum as a catalyst in a solvent such as toluene with heating at reflux (Moormann, A. E. et al *J. Med. Chem.* 1990, 33, 614-626). The esters 2 are prepared using the procedures known in the art. Treatment of the imidazoline 3 with phosgene in the presence of a base such as triethylamine gives the racemic carbamoyl chloride 4. Coupling of the racemic carbamoyl chloride 4 with appropriate R amine groups provides the compounds of the formula I as racemic mixtures. Many R amine groups are commercially available. If it is desired, R amine groups can be prepared using synthetic methods known in the art. Suitable processes for making these R amine groups are provided in the examples.

If it is desired to prepare the optically active compounds of formula I, the enantiomers of the carbamoyl chloride rac-4 can be separated using chiral chromatography. The chiral stationary phase R,R-Whelk-O1, available through Regis Technologies, can be used. Coupling of the desired enantiomer 5A with appropriate R amine groups provides the optically active compounds of the formula I.

Also the optically active compounds of formula I can be obtained by chiral separation of the racemic mixtures of 1. The chiral stationary phase Diacel ChiralPak OD or AD can be used.

The absolute stereochemistry of the preferred enantiomer of I is determined based on the crystal structure of its complex with the human MDM2 (Vassilev et al. *Science,* 2004, 303, 844-848.

The following examples and references are provided to aid the understanding of the present invention, the true scope of which is set forth in the appended claims.

Example 1 cis-4-[(4,5-Bis-(4-chloro-phenyl)-2-(2-ethoxy-pyridin-3-yl)-4,5-dihydro-imidazole-1-carbonyl]-piperazin-2-one

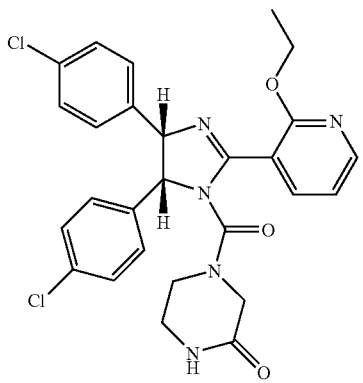

To a solution of 2-chloronicotinic acid (5 g, 31.7 mmol, Aldrich) in dimethylformamide (50 mL) were added potassium carbonate (6.579 g, 47.6 mmol) and ethyl iodide (3.8 mL, 47.7 mmol), respectively. The reaction mixture was stirred at room temperature for 3 d. Water (~50 mL) was added and the product was extracted with ethyl ether (2×75 mL). The combined organic phases were washed with brine (1×50 mL), dried over anhydrous magnesium sulfate. The solids were filtered off, and the filtrate was concentrated under reduced pressure to give 2-chloronicotinic acid ethyl ester as yellow oil. It was then dissolved in ethanol (50 mL) and sodium ethoxide (17.8 mL, 47.6 mmol, 21% in ethanol, Aldrich) was added dropwise. Precipitation was seen as sodium ethoxide was added. The reaction mixture was stirred at room temperature for 12 h. The reaction mixture was concentrated and the residue partitioned between methylene chloride (150 mL) and water (50 mL). The aqueous layer was extracted with methylene chloride (1×50 mL). The combined organic layers were washed with brine (1×20 mL) and dried over anhydrous magnesium sulfate. The solids were filtered off, and the filtrate was concentrated in vacuo. The residue was purified by flash chromatography (120 g of silica gel, 10-30% ethyl acetate in hexane) to give 2-ethoxynicotinic acid ethyl ester as an orange oil (4.04 g, 65% yield for 2 steps).

Trimethylaluminum (1.156 mL, 2.312 mmol, 2 M solution in toluene, Aldrich) was added to a flask via syringe and cooled to 0° C. A mixture of meso-1,2-bis-(4-chlorophenyl)-ethane-1,2-diamine (650 mg, 2.312 mmol, prepared according to the procedure described by Jennerwein, M. et al. *Cancer Res. Clin. Oncol* 1988, 114, 347-58; Vogtle, F.; Goldschmitt, E. *Chem. Ber.* 1976, 109, 1-40) in about 8 mL of toluene was added dropwise over a period of 30 min. After the addition was completed, the cooling bath was removed, and the mixture was stirred at room temperature for 15 min, at 50-60° C. for 30 min, and then at 80-90° C. for 30 min. When the temperature was cooled back to 60° C., a solution of 2-ethoxynicotinic acid ethyl ester (418.9 mg, 2.312 mmol) in toluene (5 mL) was added. The reaction mixture was heated at reflux for 2 h. The reaction mixture was then cooled in ice bath to 10° C., and 1 M Rochelle salt solution (10 mL) was added. The ice bath was removed, and the biphasic mixture was stirred vigorously for 30 min. Ethyl acetate (20 mL) was added and stirring was continued overnight. The layers were separated, and the organic layer was washed with brine (1×) and dried over anhydrous magnesium sulfate. The solids were filtered off, and the filtrate was concentrated in vacuo to give a yellow oil (950 mg). The crude product was purified by flash chromatography (40 g, eluting with 15% ethyl acetate in hexane, 50% ethyl acetate in hexane, then ethyl acetate) to give 4,5-bis-(4-chloro-phenyl)-2-(2-ethoxy-pyridin-3-yl)-4,5-dihydro-1H-imidazole as white solids (481 mg, 51%).

To a solution of 4,5-bis-(4-chloro-phenyl)-2-(2-ethoxy-pyridin-3-yl)-4,5-dihydro-1H-imidazole (475 mg, 1.152 mmol) and triethylamine (321 uL, 2.304 mmol) in methylene chloride (6 mL) cooled to 0° C. was added phosgene (895 uL, 1.728 mmol, 20% solution in toluene, Fluka). The reaction mixture was stirred at 0° C. for 30 min then concentrated to dryness. The residue was taken in ethyl acetate, and the solids were filtered off. The filtrate was concentrated to give crude 4,5-bis-(4-chloro-phenyl)-2-(2-ethoxy-pyridin-3-yl)-4,5-dihydro-imidazole-1-carbonyl chloride as yellow solids (450 mg).

To a solution of 4,5-bis-(4-chloro-phenyl)-2-(2-ethoxy-pyridin-3-yl)-4,5-dihydro-imidazole-1-carbonyl chloride (100 mg, 0.211 mmol) in methylene chloride (3 mL) at room temperature were added triethylamine (88 uL) and 2-piperazinone (31.7 mg, 0.317 mmol, Tyger Scientific), respectively. The reaction mixture was stirred at room temperature for 1 h. The reaction was monitored by thin layer chromatography (silica gel, 15% methanol in ethyl acetate). The reaction mixture was concentrated to dryness, and the crude residue was purified by high performance liquid chromatography (C18-silica gel, eluting with a gradient of 5-95% acetonitrile in water) to give cis-4-[(4,5-bis-(4-chloro-phenyl)-2-(2-ethoxy-pyridin-3-yl)-4,5-dihydro-imidazole-1-carbonyl]-piperazin-2-one as white solid (98 mg, 86%). HR-MS (ES, m/z) calculated for $C_{27}H_{26}N_5O_3Cl_2[(M+H)^+]$ 538.1407, observed 538.1408.

Example 2 cis-2-{4-[4,5-Bis-(4-chloro-phenyl)-2-(2-ethoxy-pyridin-3-yl)-4,5-dihydro-imidazole-1-carbonyl]-piperazin-1-yl}-N,N-dimethyl-acetamide

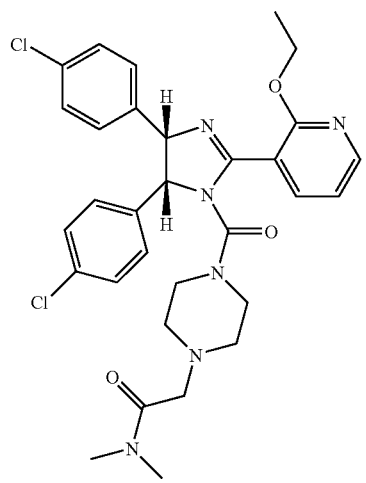

4,5-Bis-(4-chloro-phenyl)-2-(2-ethoxy-pyridin-3-yl)-4,5-dihydro-imidazole-1-carbonyl chloride (example 1) was reacted with N,N-dimethyl-2-piperazin-1-yl-acetamide (Oakwood Products) to give cis-2-{4-[4,5-bis-(4-chloro-phenyl)-2-(2-ethoxy-pyridin-3-yl)-4,5-dihydro-imidazole-1-carbonyl]-piperazin-1-yl}-N,N-dimethyl-acetamide in an analogous manner as described in example 1. HR-MS (ES, m/z) calculated for $C_{31}H_{35}N_6O_3Cl_2$ $[(M+H)^+]$ 609.2142, observed 609.2146.

Example 3 cis-[4,5-Bis-(4-chloro-phenyl)-2-(2-ethoxy-pyridin-3-yl)-4,5-dihydro-imidazol-1-yl]-[4-(2-methanesulfonyl-ethyl)-piperazin-1-yl]-methanone

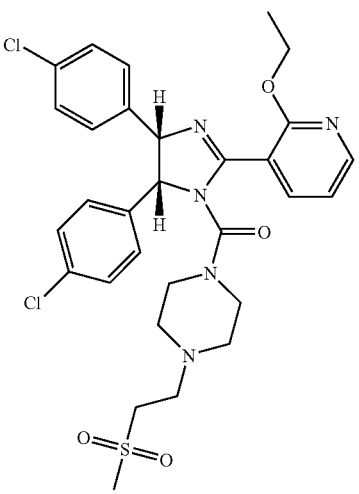

Methyl vinyl sulfone (1.8 mL, 20.1 mmol) was added to a solution of 1-(tert-butyloxycarbonyl)piperazine (1.50 g, 8 mmol) in methanol (84 mL). The reaction mixture was stirred at room temperature for 4 h and concentrated to a white solid. Purification of the solid by flash column chromatography (silica gel, eluting with 1-5% methanol in methylene chloride) gave 1-tert-butyloxycarbonyl-4-(2-methanesulfonyl-ethyl)piperazine as a white solid (2.29 g, 95%).

Hydrochloric acid (42 mL, 168 mmol, 4 M in 1,4-dioxane) was added to a cooled solution of 1-tert-butyloxycarbonyl-4-(2-methanesulfonylethyl)piperazine (2.29 g, 7.8 mmol) in 1,4-dioxane (42 mL). The mixture was stirred at room temperature overnight then concentrated to give 1-(2-methanesulfonylethyl)piperazine dihydrochloride as a white solid (2.05 g).

4,5-Bis-(4-chloro-phenyl)-2-(2-ethoxy-pyridin-3-yl)-4,5-dihydro-imidazole-1-carbonyl chloride (example 1) was reacted with 1-(2-methanesulfonylethyl)piperazine dihydrochloride to give cis-[4,5-bis-(4-chloro-phenyl)-2-(2-ethoxy-pyridin-3-yl)-4,5-dihydro-imidazol-1-yl]-[4-(2-methanesulfonyl-ethyl)-piperazin-1-yl]-methanone in an analogous manner as described in example 1. HR-MS (ES, m/z) calculated for $C_{30}H_{34}N_5O_4SCl_2$ [(M+H)$^+$] 630.1703, observed 603.1705.

Example 4 cis-2-{4-[4,5-Bis-(4-chloro-phenyl)-2-(2-ethoxy-pyridin-3-yl)-4,5-dihydro-imidazole-1-carbonyl]-piperazin-1-yl}-1-morpholin-4-yl-ethanone

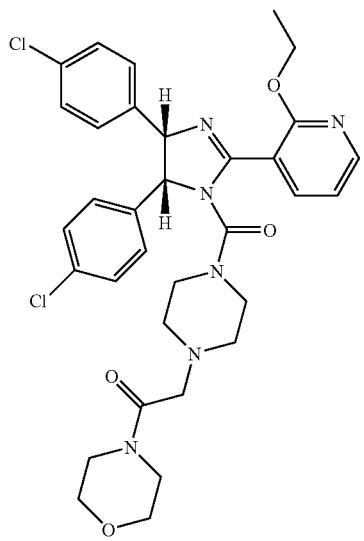

4,5-Bis-(4-chloro-phenyl)-2-(2-ethoxy-pyridin-3-yl)-4,5-dihydro-imidazole-1-carbonyl chloride (example 1) was reacted with 1-morpholin-4-yl-2-piperazin-1-yl-ethanone (Oakwood Products) to give cis-2-{4-[4,5-bis-(4-chloro-phenyl)-2-(2-ethoxy-pyridin-3-yl)-4,5-dihydro-imidazole-1-carbonyl]-piperazin-1-yl}-1-morpholin-4-yl-ethanone in an analogous manner as described in example 1. HR-MS (ES, m/z) calculated for $C_{33}H_{37}N_6O_4Cl_2$ [(M+H)$^+$] 651.2248, observed 651.2250.

Example 5 cis-4-[4,5-Bis-(4-chloro-phenyl)-2-(4-ethoxy-2-trifluoromethyl-pyrimidin-5-yl)-4,5-dihydro-imidazole-1-carbonyl]-piperazin-2-one

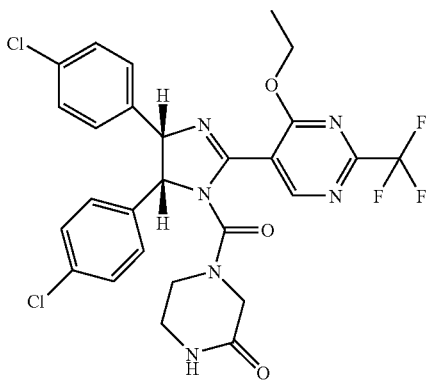

4-Hydroxy-2-trifluoromethyl-pyrimidine-5-carboxylic acid (1 g, 4.828 mmol, Oakwood Products) was dissolved in dimethylformamide (10 mL) and potassium carbonate (1.668 g, 12.070 mmol) was added. After stirring at room temperature for 15 min, iodoethane (0.966 mL, 12.070 mmol) was added and the reaction mixture was stirred at room temperature for 3 d. Water was added, and the product was extracted with ethyl acetate (2×). The organic layers were washed with water (1×), brine (1×) and dried over anhydrous sodium sulfate. The solids were filtered off, and the filtrate was concentrated in vacuo. Purification of the residue by flash column chromatography (silica gel, eluting with a gradient of 5-50% ethyl acetate in hexanes) to give 4-ethoxy-2-trifluoromethyl-pyrimidine-5-carboxylic acid ethyl ester (852 mg, 67%).

4-Ethoxy-2-trifluoromethyl-pyrimidine-5-carboxylic ethyl ester was reacted with meso-1,2-bis-(4-chlorophenyl)-ethane-1,2-diamine in an analogous manner as described in example 1 to give cis-4-[4,5-bis-(4-chloro-phenyl)-2-(4-ethoxy-2-trifluoromethyl-pyrimidin-5-yl)-4,5-dihydro-1H-imidazole. HR-MS (ES, m/z) calculated for $C_{22}H_{18}N_4OF_3Cl_2$ [(M+H)$^+$] 481.0805, observed 481.0806.

Using the procedure as described in example 1, cis-4-[4,5-bis-(4-chloro-phenyl)-2-(4-ethoxy-2-trifluoromethyl-pyrimidin-5-yl)-4,5-dihydro-1H-imidazole was reacted with phosgene to give cis-4-[4,5-bis-(4-chloro-phenyl)-2-(4-ethoxy-2-trifluoromethyl-pyrimidin-5-yl)-4,5-dihydro-imidazole-1-carbonyl chloride. The carbonyl chloride was then coupled with 2-piperazinone to give cis-4-[4,5-bis-(4-chloro-phenyl)-2-(4-ethoxy-2-trifluoromethyl-pyrimidin-5-yl)-4,5-dihydro-imidazole-1-carbonyl]-piperazin-2-one. HR-MS (ES, m/z) calculated for $C_{27}H_{24}N_6O_3F_3Cl_2$ [(M+H)$^+$] 607.1234, observed 607.1231.

Example 6 cis-[4,5-Bis-(4-chloro-phenyl)-2-(4-ethoxy-2-trifluoromethyl-pyrimidin-5-yl)-4,5-dihydro-imidazol-1-yl]-[4-(2-methanesulfonyl-ethyl)-piperazin-1-yl]-methanone

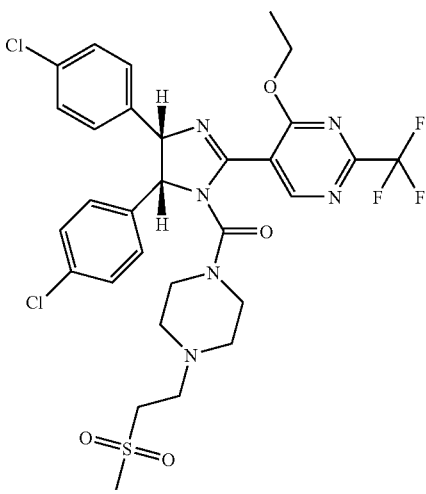

cis-4-[4,5-Bis-(4-chloro-phenyl)-2-(4-ethoxy-2-trifluoromethyl-pyrimidin-5-yl)-4,5-dihydro-imidazole-1-carbonyl chloride (example 5) was reacted with 1-(2-methanesulfonylethyl)piperazine dihydrochloride (example 3) to give cis-[4,5-bis-(4-chloro-phenyl)-2-(4-ethoxy-2-trifluoromethyl-pyrimidin-5-yl)-4,5-dihydro-imidazol-1-yl]-[4-(2-methanesulfonyl-ethyl)-piperazin-1-yl]-methanone in an analogous manner as described in example 1. HR-MS (ES, m/z) calculated for $C_{30}H_{32}N_6O_4SF_3Cl_2$ [(M+H)$^+$] 699.1530, observed 699.1533.

Example 7 cis-2-{4-[4,5-Bis-(4-chloro-phenyl)-2-(4-ethoxy-2-trifluoromethyl-pyrimidin-5-yl)-4,5-dihydro-imidazole-1-carbonyl]-piperazin-1-yl}-1-morpholin-4-yl-ethanone

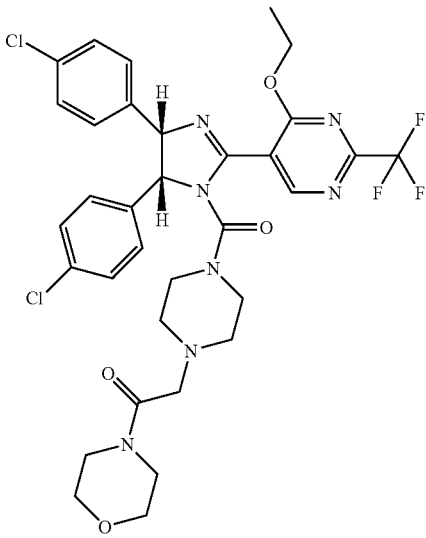

cis-4-[4,5-Bis-(4-chloro-phenyl)-2-(4-ethoxy-2-trifluoromethyl-pyrimidin-5-yl)-4,5-dihydro-imidazole-1-carbonyl chloride (example 5) was reacted with 1-morpholin-4-yl-2-piperazin-1-yl-ethanone (Oakwood Products) to give cis-2-{4-[4,5-bis-(4-chloro-phenyl)-2-(4-ethoxy-2-trifluoromethyl-pyrimidin-5-yl)-4,5-dihydro-imidazole-1-carbonyl]-piperazin-1-yl}-1-morpholin-4-yl-ethanone in an analogous manner as described in example 1. HR-MS (ES, m/z) calculated for $C_{33}H_{35}N_7O_4F_3Cl_2$ [(M+H)$^+$] 720.2074, observed 720.2075.

Example 8 cis-4-[4,5-Bis-(4-chloro-phenyl)-2-(2,4-diethoxy-pyrimidin-5-yl)-4,5-dihydro-imidazole-1-carbonyl]-piperazin-2-one

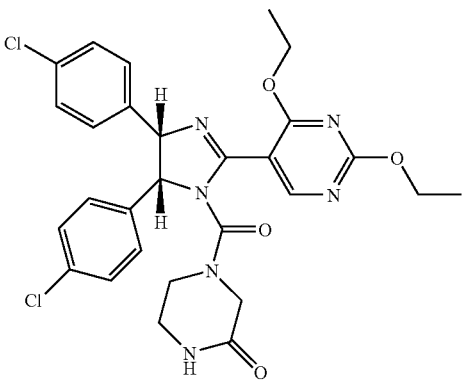

To a solution of ethyl 4-chloro-5-pyrimidine carboxylate (5 g, 21.488 mmol, Aldrich) in ethanol (50 mL) was added sodium ethoxide dropwise (12 mL, 32.232 mmol, 21% solution in ethanol, Aldrich). Precipitation was seen as sodium ethoxide was added. The reaction mixture was stirred at room temperature for 12 h. The reaction mixture was then heated at ~60° C. for 2 h. The reaction mixture was then diluted with ethyl acetate, washed with water, brine, and dried over magnesium sulfate. The solids were filtered off and the filtrate was concentrated in vacuo. The residue was purified by flash chromatography (120 g of silica gel, gradient of 10-50% ethyl acetate in hexane) to give 2,4-diethoxy-pyrimidine-5-carboxylic ethyl ester (1.679 g) and 4-ethoxy-2-methylsulfanyl-pyrimidine-5-carboxylic acid ethyl ester (1.764 g).

2,4-Diethoxy-pyrimidine-5-carboxylic ethyl ester was reacted with meso-1,2-bis-(4-chlorophenyl)-ethane-1,2-diamine in an analogous manner as described in example 1 to give cis-4-[4,5-bis-(4-chloro-phenyl)-2-(2,4-diethoxy-pyrimidin-5-yl)-4,5-dihydro-1H-imidazole. HR-MS (ES, m/z) calculated for $C_{23}H_{23}N_4O_2Cl_2$ [(M+H)$^+$] 457.1193, observed 457.1193.

Using the procedure as described in example 1, cis-4-[4,5-bis-(4-chloro-phenyl)-2-(2,4-diethoxy-pyrimidin-5-yl)-4,5-dihydro-1H-imidazole was reacted with phosgene to give cis-4-[4,5-bis-(4-chloro-phenyl)-2-(2,4-diethoxy-pyrimidin-5-yl)-4,5-dihydro-imidazole-1-carbonyl chloride. The carbonyl chloride was then coupled with 2-piperazinone (Alfa) to give cis-4-[4,5-bis-(4-chloro-phenyl)-2-(2,4-diethoxy-pyrimidin-5-yl)-4,5-dihydro-imidazole-1-carbonyl]-piperazin-2-one. HR-MS (ES, m/z) calculated for $C_{28}H_{29}N_6O_4Cl_2$ [(M+H)$^+$] 583.1622, observed 583.1621.

Example 9
cis-2-{4-[4,5-Bis-(4-chloro-phenyl)-2-(2,4-diethoxy-pyrimidin-5-yl)-4,5-dihydro-imidazole-1-carbonyl]-piperazin-1-yl}-N,N-dimethyl-acetamide

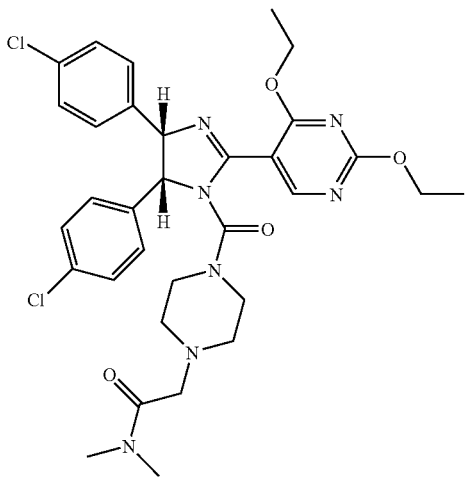

cis-4-[4,5-Bis-(4-chloro-phenyl)-2-(2,4-diethoxy-pyrimidin-5-yl)-4,5-dihydro-imidazole-1-carbonyl chloride (example 8) was reacted with N,N-dimethyl-2-piperazin-1-yl-acetamide (Oakwood Products) to give cis-2-{4-[4,5-bis-(4-chloro-phenyl)-2-(2,4-diethoxy-pyrimidin-5-yl)-4,5-dihydro-imidazole-1-carbonyl]-piperazin-1-yl}-N,N-dimethyl-acetamide in an analogous manner as described in example 1. HR-MS (ES, m/z) calculated for $C_{32}H_{37}N_7O_4Cl_2$ [(M+H)$^+$] 654.2357, observed 654.2355.

Example 10
cis-[4,5-Bis-(4-chloro-phenyl)-2-(2,4-diethoxy-pyrimidin-5-yl)-4,5-dihydro-imidazol-1-yl]-[4-(2-methanesulfonyl-ethyl)-piperazin-1-yl]-methanone

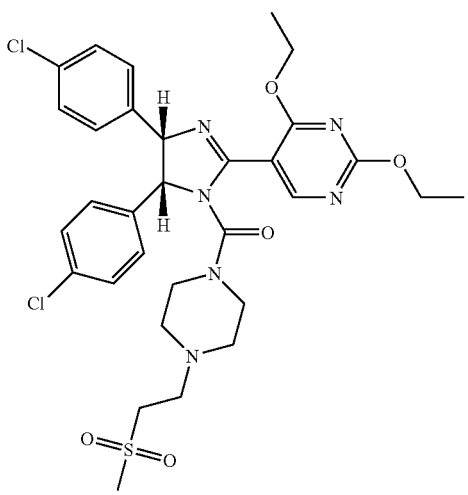

cis-4-[4,5-Bis-(4-chloro-phenyl)-2-(2,4-diethoxy-pyrimidin-5-yl)-4,5-dihydro-imidazole-1-carbonyl chloride (example 8) was reacted with 1-(2-methanesulfonylethyl)-piperazine dihydrochloride (example 3) to give cis-[4,5-bis-(4-chloro-phenyl)-2-(2,4-diethoxy-pyrimidin-5-yl)-4,5-dihydro-imidazol-1-yl]-[4-(2-methanesulfonyl-ethyl)-piperazin-1-yl]-methanone in an analogous manner as described in example 1. HR-MS (ES, m/z) calculated for $C_{31}H_{37}N_6O_5SCl_2$ [(M+H)$^+$] 675.1918, observed 675.1914.

Example 11
cis-2-{-[4,5-Bis-(4-chloro-phenyl)-2-(2,4-diethoxy-pyrimidin-5-yl)-4,5-dihydro-imidazole-1-carbonyl]-piperazin-1-yl}-1-morpholin-4-yl-ethanone

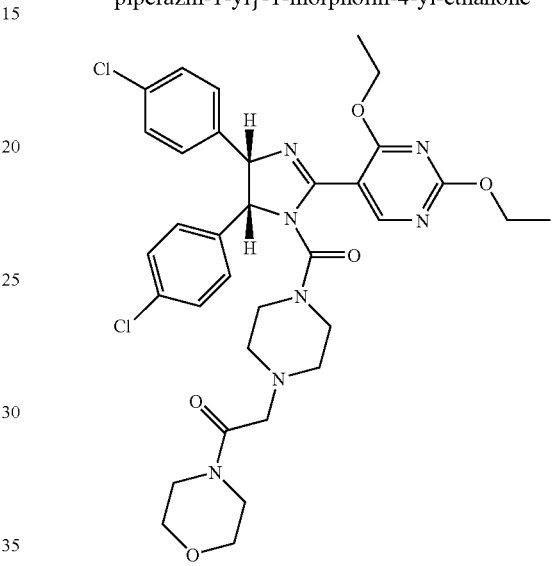

cis-4-[4,5-Bis-(4-chloro-phenyl)-2-(2,4-diethoxy-pyrimidin-5-yl)-4,5-dihydro-imidazole-1-carbonyl chloride (example 8) was reacted with 1-morpholin-4-yl-2-piperazin-1-yl-ethanone (Oakwood Products) to give cis-2-{4-[4,5-bis-(4-chloro-phenyl)-2-(2,4-diethoxy-pyrimidin-5-yl)-4,5-dihydro-imidazole-1-carbonyl]-piperazin-1-yl}-1-morpholin-4-yl-ethanone in an analogous manner as described in example 1. HR-MS (ES, m/z) calculated for $C_{34}H_{40}N_7O_5Cl_2$ [(M+H)$^+$] 696.2463, observed 696.2463.

Example 12
cis-4-[4,5-Bis-(4-chloro-phenyl)-2-(4-ethoxy-2-methylsulfanyl-pyrimidin-5-yl)-4,5-dihydro-imidazole-1-carbonyl]-piperazin-2-one

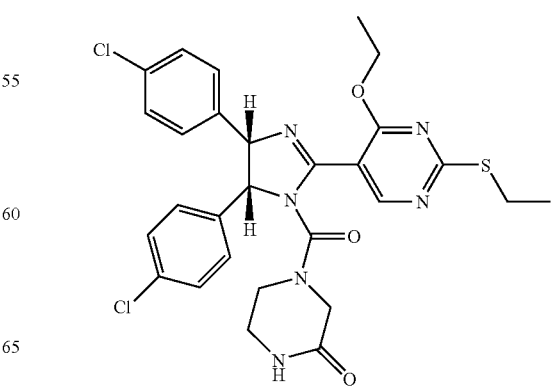

4-Ethoxy-2-methylsulfanyl-pyrimidine-5-carboxylic acid ethyl ester (example 8) was reacted with meso-1,2-bis-(4-chlorophenyl)-ethane-1,2-diamine in an analogous manner as described in example 1 to give cis-4-[4,5-bis-(4-chloro-phenyl)-2-(4-ethoxy-2-methyl-sulfanyl-pyrimidin-5-yl)-4,5-dihydro-1H-imidazole. HR-MS (ES, m/z) calculated for $C_{22}H_{21}N_4OSCl_2$ [(M+H)$^+$] 459.0808, observed 459.0808.

Using the procedure as described in example 1, cis-4-[4,5-bis-(4-chloro-phenyl)-2-(4-ethoxy-2-methylsulfanyl-pyrimidin-5-yl)-4,5-dihydro-1H-imidazole was reacted with phosgene to give cis-4-[4,5-bis-(4-chloro-phenyl)-2-(4-ethoxy-2-methylsulfanyl-pyrimidin-5-yl)-4,5-dihydro-imidazole-1-carbonyl chloride. The carbonyl chloride was then coupled with 2-piperazinone (Alfa) to give cis-4-[4,5-bis-(4-chloro-phenyl)-2-(4-ethoxy-2-methylsulfanyl-pyrimidin-5-yl)-4,5-dihydro-imidazole-1-carbonyl]-piperazin-2-one. HR-MS (ES, m/z) calculated for $C_{27}H_{27}N_6O_3SCl_2$ [(M+H)$^+$] 585.1237, observed 585.1236.

Example 13 cis-2-{4-[4,5-Bis-(4-chloro-phenyl)-2-(4-ethoxy-2-methylsulfanyl-pyrimidin-5-yl)-4,5-dihydro-imidazole-1-carbonyl]-piperazin-1-yl}-N,N-dimethyl-acetamide

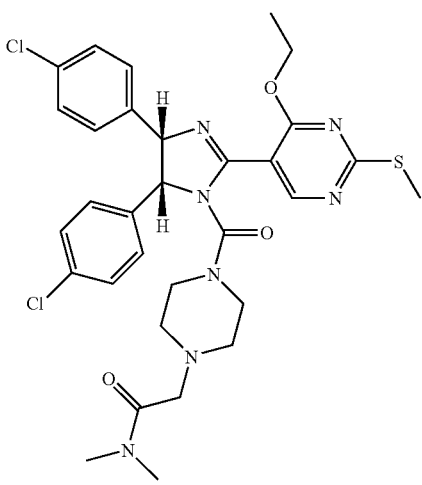

cis-4-[4,5-Bis-(4-chloro-phenyl)-2-(4-ethoxy-2-methyl-sulfanyl-pyrimidin-5-yl)-4,5-dihydro-imidazole-1-carbonyl chloride (example 12) was reacted with N,N-dimethyl-2-piperazin-1-yl-acetamide (Oakwood Products) to give cis-2-{4-[4,5-bis-(4-chloro-phenyl)-2-(4-ethoxy-2-methylsulfanyl-pyrimidin-5-yl)-4,5-dihydro-imidazole-1-carbonyl]-piperazin-1-yl}-N,N-dimethyl-acetamide in an analogous manner as described in example 1. HR-MS (ES, m/z) calculated for $C_{31}H_{36}N_7O_3SCl_2$ [(M+H)$^+$] 656.1972, observed 656.1973.

Example 14 cis-4,5-Bis-(4-chloro-phenyl)-2-(4-ethoxy-2-methylsulfanyl-pyrimidin-5-yl)-4,5-dihydro-imidazol-1-yl]-[4-(2-methanesulfonyl-ethyl)-piperazin-1-yl]-methanone

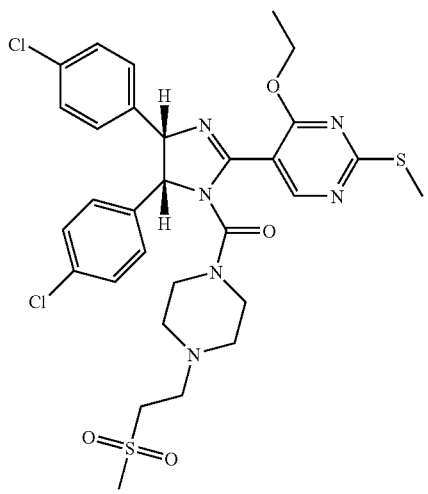

cis-4-[4,5-Bis-(4-chloro-phenyl)-2-(4-ethoxy-2-methyl-sulfanyl-pyrimidin-5-yl)-4,5-dihydro-imidazole-1-carbonyl chloride (example 12) was reacted with 1-(2-methanesulfonylethyl)-piperazine dihydrochloride (example 3) to give cis-[4,5-bis-(4-chloro-phenyl)-2-(4-ethoxy-2-methylsulfanyl-pyrimidin-5-yl)-4,5-dihydro-imidazol-1-yl]-[4-(2-methanesulfonyl-ethyl)-piperazin-1-yl]-methanone in an analogous manner as described in example 1. HR-MS (ES, m/z) calculated for $C_{30}H_{35}N_6O_4S_2Cl_2$ [(M+H)$^+$] 677.1533, observed 677.1532.

Example 15 cis-2-{4-[4,5-Bis-(4-chloro-phenyl)-2-(4-ethoxy-2-methylsulfanyl-pyrimidin-5-yl)-4,5-dihydro-imidazole-1-carbonyl]-piperazin-1-yl}-1-morpholin-4-yl-ethanone

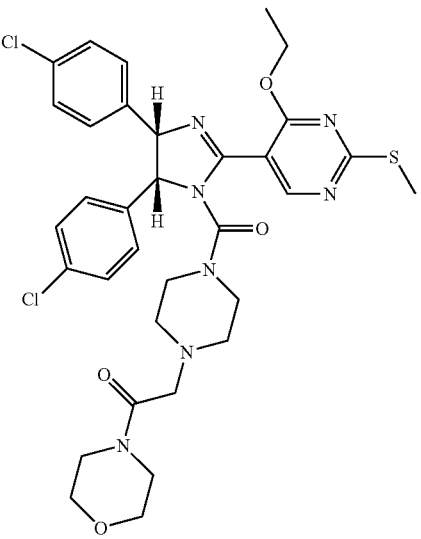

cis-4-[4,5-Bis-(4-chloro-phenyl)-2-(4-ethoxy-2-methyl-sulfanyl-pyrimidin-5-yl)-4,5-dihydro-imidazole-1-carbonyl chloride (example 12) was reacted with 1-morpholin-4-yl-2-piperazin-1-yl-ethanone (Oakwood Products) to give cis-2-{4-[4,5-bis-(4-chloro-phenyl)-2-(4-ethoxy-2-methylsulfanyl-pyrimidin-5-yl)-4,5-dihydro-imidazole-1-carbonyl]-piperazin-1-yl}-1-morpholin-4-yl-ethanone in an analogous manner as described in example 1. HR-MS (ES, m/z) calculated for $C_{33}H_{38}N_7O_4SCl_2$ [(M+H)$^+$] 698.2078, observed 698.2078.

Example 16 cis-4-[4,5-Bis-(4-chloro-phenyl)-2-(4-ethoxy-2-methyl-pyrimidin-5-yl)-4,5-dihydro-imidazole-1-carbonyl]-piperazin-2-one

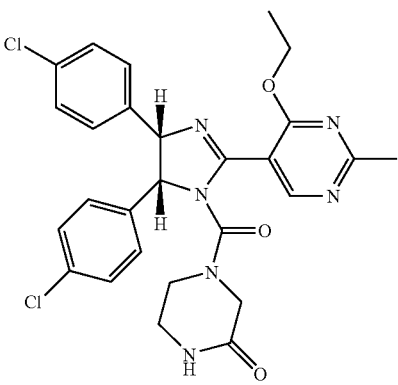

4-Ethoxy-2-methyl-pyrimidine-5-carboxylic acid ethyl ester (prepared according to the procedures described by Baxter, R. L. et al. *J. Chem. Soc. Perkin Trans.*/1990, 2963-2966 and Dostert, P. et al. *Eur. J. Med. Chem.* 1982, 17, 437-444) was reacted with meso-1,2-bis-(4-chlorophenyl)-ethane-1,2-diamine in an analogous manner as described in example 1 to give cis-4-[4,5-bis-(4-chloro-phenyl)-2-(4-ethoxy-2-methyl-pyrimidin-5-yl)-4,5-dihydro-1H-imidazole. HR-MS (ES, m/z) calculated for $C_{22}H_{21}N_4OSCl_2$ [(M+H)$^+$] 459.0808, observed 459.0808.

Using the procedure as described in example 1, cis-4-[4,5-bis-(4-chloro-phenyl)-2-(4-ethoxy-2-methyl-pyrimidin-5-yl)-4,5-dihydro-1H-imidazole was reacted with phosgene to give cis-4-[4,5-bis-(4-chloro-phenyl)-2-(4-ethoxy-2-methyl-pyrimidin-5-yl)-4,5-dihydro-imidazole-1-carbonyl chloride. The carbonyl chloride was then coupled with 2-piperazinone (Alfa) to give cis-4-[4,5-bis-(4-chloro-phenyl)-2-(4-ethoxy-2-methyl-pyrimidin-5-yl)-4,5-dihydro-imidazole-1-carbonyl]-piperazin-2-one. HR-MS (ES, m/z) calculated for $C_{27}H_{27}N_6O_3Cl_2$ [(M+H)$^+$] 553.1516, observed 553.1515.

Example 17 cis-2-{4-[4,5-Bis-(4-chloro-phenyl)-2-(4-ethoxy-2-methyl-pyrimidin-5-yl)-4,5-dihydro-imidazole-1-carbonyl]-piperazin-1-yl}-N,N-dimethyl-acetamide

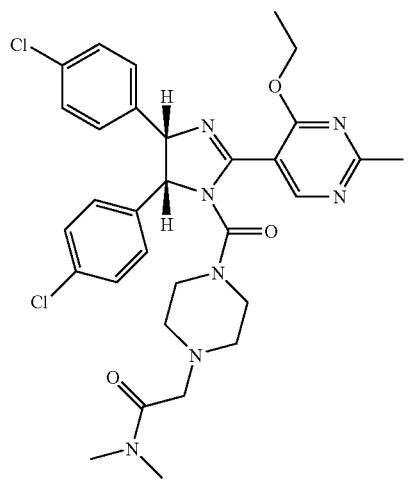

cis-4-[4,5-Bis-(4-chloro-phenyl)-2-(4-ethoxy-2-methyl-pyrimidin-5-yl)-4,5-dihydro-imidazole-1-carbonyl chloride (example 16) was reacted with N,N-dimethyl-2-piperazin-1-yl-acetamide (Oakwood Products) to give cis-4-[4,5-bis-(4-chloro-phenyl)-2-(4-ethoxy-2-methyl-pyrimidin-5-yl)-4,5-dihydro-imidazole-1-carbonyl]-piperazin-1-yl}-N,N-dimethyl-acetamide in an analogous manner as described in example 1. HR-MS (ES, m/z) calculated for $C_{31}H_{36}N_7O_3Cl_2$ [(M+H)$^+$] 624.2251, observed 624.2253.

Example 18 cis-[4,5-Bis-(4-chloro-phenyl)-2-(4-ethoxy-2-methyl-pyrimidin-5-yl)-4,5-dihydro-imidazol-1-yl]-[4-(2-methanesulfonyl-ethyl)-piperazin-1-yl]-methanone

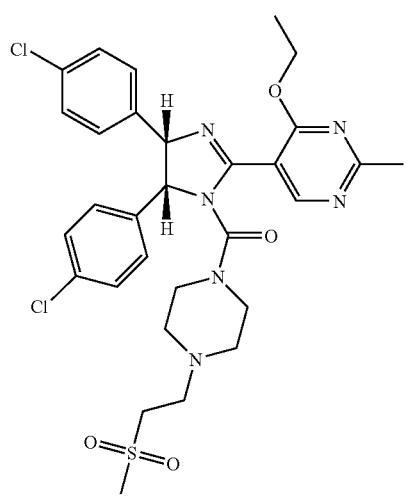

cis-4-[4,5-Bis-(4-chloro-phenyl)-2-(4-ethoxy-2-methyl-pyrimidin-5-yl)-4,5-dihydro-imidazole-1-carbonyl chloride (example 16) was reacted with 1-(2-methanesulfonyl-ethyl)piperazine dihydrochloride (example 3) to give cis-[4,5-bis-(4-chloro-phenyl)-2-(4-ethoxy-2-methyl-pyrimidin-5-yl)-4,5-dihydro-imidazol-1-yl]-[4-(2-methanesulfonyl-ethyl)-piperazin-1-yl]-methanone in an analogous manner as described in example 1. HR-MS (ES, m/z) calculated for $C_{30}H_{34}N_6O_4SCl_2$ [(M+H)$^+$] 645.1812, observed 645.1814.

Example 19 cis-2-{4-[4,5-Bis-(4-chloro-phenyl)-2-(4-ethoxy-2-methyl-pyrimidin-5-yl)-4,5-dihydro-imidazole-1-carbonyl]-piperazin-1-yl}-1-morpholin-4-yl-ethanone

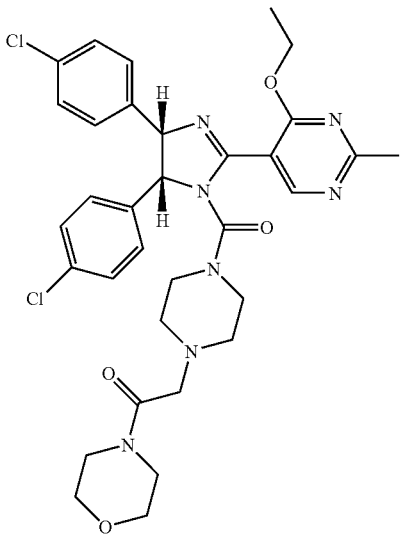

cis-4-[4,5-Bis-(4-chloro-phenyl)-2-(4-ethoxy-2-methyl-pyrimidin-5-yl)-4,5-dihydro-imidazole-1-carbonyl chloride (example 16) was reacted with 1-morpholin-4-yl-2-piperazin-1-yl-ethanone (Oakwood Products) to give cis-2-{4-[4,5-bis-(4-chloro-phenyl)-2-(4-ethoxy-2-methyl-pyrimidin-5-yl)-4,5-dihydro-imidazole-1-carbonyl]-piperazin-1-yl}-1-morpholin-4-yl-ethanone in an analogous manner as described in example 1. HR-MS (ES, m/z) calculated for $C_{33}H_{38}N_7O_4Cl_2$ [(M+H)$^+$] 666.2357, observed 666.2358.

Example 20 cis-4-[2-(2-tert-Butyl-4-ethoxy-pyrimidin-5-yl)-4,5-bis-(4-chloro-phenyl)-4,5-dihydro-imidazole-1-carbonyl]-piperazin-2-one hydrochloride

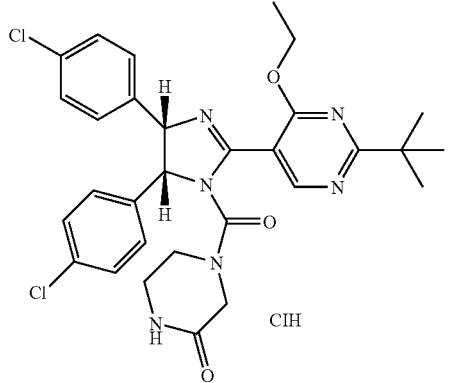

A solution of 4-hydroxy-2-tert-butyl-pyrimidine-5-carboxylic acid ethyl ester (3 g, 13.377 mmol, prepared in an analogous manner as described for the preparation of 2-ethyl-4-hydroxy-pyrimidine-5-carboxylic acid ethyl ester, Dostert, P. et al. Eur. J. Med. Chem. 1982, 17, 437-444) in dimethylformamide (10 mL) was added slowly to the suspension of sodium hydride (800 mg, 60% in mineral oil, Aldrich) in dimethylformamide cooled to 0° C. After the addition, the ice bath was removed and the reaction mixture was stirred at room temperature for 2 h. The reaction mixture was stirred at room temperature for 4 h then quenched with saturated solution of ammonium chloride. It was extracted with ethyl acetate (2×). The organic extracts were washed with brine (1×), dried over anhydrous sodium sulfate and concentrated. Purification of the crude residue by flash column chromatography (120 g of silica gel, eluting with a gradient of 5-60% ethyl acetate in hexane gave 4-ethoxy-2-tert-butyl-pyrimidine-5-carboxylic acid ethyl ester (1.12 g, 30%).

2-tert-Butyl-4-ethoxy-pyrimidine-5-carboxylic acid ethyl ester was reacted with meso-1,2-bis-(4-chlorophenyl)-ethane-1,2-diamine in an analogous manner as described in example 1 to give cis-4-[2-(2-tert-butyl-4-ethoxy-pyrimidin-5-yl)-4,5-bis-(4-chloro-phenyl)-4,5-dihydro-1H-imidazole. HR-MS (ES, m/z) calculated for $C_{22}H_{21}N_4OSCl_2$ [(M+H)$^+$] 459.0808, observed 459.0808.

Using the procedure as described in example 1, cis-4-[2-(2-tert-butyl-4-ethoxy-pyrimidin-5-yl)-4,5-bis-(4-chloro-phenyl)-4,5-dihydro-1H-imidazole was reacted with phosgene to give cis-4-[2-(2-tert-butyl-4-ethoxy-pyrimidin-5-yl)-4,5-bis-(4-chloro-phenyl)-4,5-dihydro-imidazole-1-carbonyl chloride. The carbonyl chloride was then coupled with 2-piperazinone (Alfa) to give cis-4-[2-(2-tert-butyl-4-ethoxy-pyrimidin-5-yl)-4,5-bis-(4-chloro-phenyl)-4,5-dihydro-imidazole-1-carbonyl]-piperazin-2-one hydrochloride. HR-MS (ES, m/z) calculated for $C_{30}H_{33}N_6O_3Cl_2$ [(M+H)$^+$] 595.1986, observed 595.1985.

Example 21 cis-2-{4-[2-(2-tert-Butyl-4-ethoxy-pyrimidin-5-yl)-4,5-bis-(4-chloro-phenyl)-4,5-dihydro-imidazole-1-carbonyl]-piperazin-1-yl}-N,N-dimethyl-acetamide hydrochloride

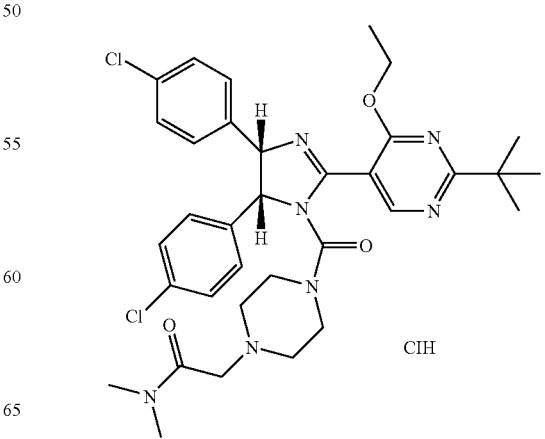

cis-4-[2-(2-tert-Butyl-4-ethoxy-pyrimidin-5-yl)-4,5-bis-(4-chloro-phenyl)-4,5-dihydro-imidazole-1-carbonyl chloride (example 20) was reacted with N,N-dimethyl-2-piperazin-1-yl-acetamide (Oakwood Products) to give cis-2-{4-[2-(2-tert-butyl-4-ethoxy-pyrimidin-5-yl)-4,5-bis-(4-chlorophenyl)-4,5-dihydro-imidazole-1-carbonyl]-piperazin-1-yl}-N,N-dimethyl-acetamide hydrochloride in an analogous manner as described in example 1. HR-MS (ES, m/z) calculated for $C_{34}H_{42}N_7O_3Cl_2$ [(M+H)$^+$] 666.2721, observed 666.2721.

Example 22
cis-[2-(2-tert-Butyl-4-ethoxy-pyrimidin-5-yl)-4,5-bis-(4-chloro-phenyl)-4,5-dihydro-imidazol-1-yl]-[4-(2-methanesulfonyl-ethyl)-piperazin-1-yl]-methanone hydrochloride

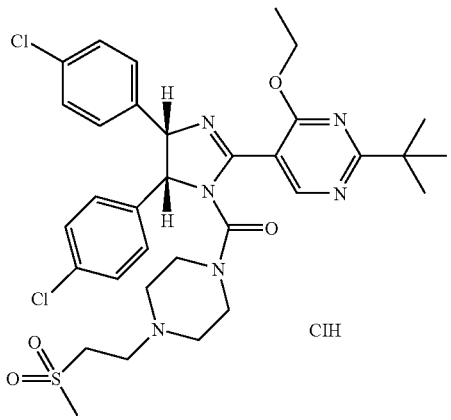

cis-4-[2-(2-tert-Butyl-4-ethoxy-pyrimidin-5-yl)-4,5-bis-(4-chloro-phenyl)-4,5-dihydro-imidazole-1-carbonyl chloride (example 20) was reacted with 1-(2-methanesulfonyl-ethyl)piperazine dihydrochloride (example 3) to give cis-[2-(2-tert-butyl-4-ethoxy-pyrimidin-5-yl)-4,5-bis-(4-chlorophenyl)-4,5-dihydro-imidazol-1-yl]-[4-(2-methanesulfonyl-ethyl)-piperazin-1-yl]-methanone hydrochloride in an analogous manner as described in example 1. HR-MS (ES, m/z) calculated for $C_{33}H_{41}N_6O_4SCl_2$ [(M+H)$^+$] 687.2282, observed 687.2286.

Example 23
cis-2-{4-[2-(2-tert-Butyl-4-ethoxy-pyrimidin-5-yl)-4,5-bis-(4-chloro-phenyl)-4,5-dihydro-imidazole-1-carbonyl]-piperazin-1-yl}-1-morpholin-4-yl-ethanone

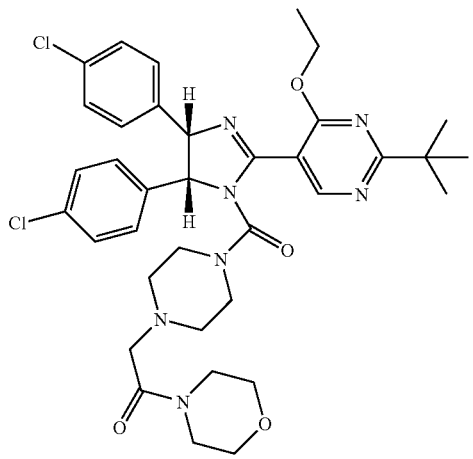

cis-4-[2-(2-tert-Butyl-4-ethoxy-pyrimidin-5-yl)-4,5-bis-(4-chloro-phenyl)-4,5-dihydro-imidazole-1-carbonyl chloride (example 20) was reacted with 1-morpholin-4-yl-2-piperazin-1-yl-ethanone (Oakwood Products) to give cis-2-{4-[2-(2-tert-butyl-4-ethoxy-pyrimidin-5-yl)-4,5-bis-(4-chlorophenyl)-4,5-dihydro-imidazole-1-carbonyl]-piperazin-1-yl}-1-morpholin-4-yl-ethanone in an analogous manner as described in example 1. HR-MS (ES, m/z) calculated for $C_{36}H_{44}N_7O_4Cl_2$ [(M+H)$^+$] 708.2827, observed 708.2830.

Example 24
cis-[2-(2-tert-Butyl-4-ethoxy-pyrimidin-5-yl)-4,5-bis-(4-chloro-phenyl)-4,5-dihydro-imidazol-1-yl]-(4-dimethylamino-piperidin-1-yl)-methanone

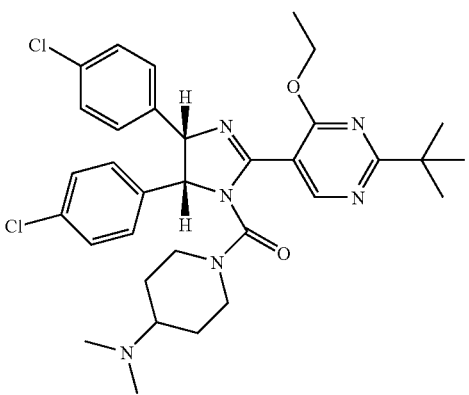

cis-4-[2-(2-tert-Butyl-4-ethoxy-pyrimidin-5-yl)-4,5-bis-(4-chloro-phenyl)-4,5-dihydro-imidazole-1-carbonyl chloride (example 20) was reacted 4-dimethylamino-piperidine (Aldrich) to give cis-[2-(2-tert-butyl-4-ethoxy-pyrimidin-5-yl)-4,5-bis-(4-chloro-phenyl)-4,5-dihydro-imidazol-1-yl]-(4-dimethylamino-piperidin-1-yl)-methanone in an analogous manner as described in example 1. HR-MS (ES, m/z) calculated for $C_{33}H_{41}N_6O_2Cl_2$ [(M+H)$^+$] 623.2663, observed 623.2665.

Example 25
cis-[2-(2-tert-Butyl-4-ethoxy-pyrimidin-5-yl)-4,5-bis-(4-chloro-phenyl)-4,5-dihydro-imidazol-1-yl]-(4-pyrrolidin-1-yl-piperidin-1-yl)-methanone

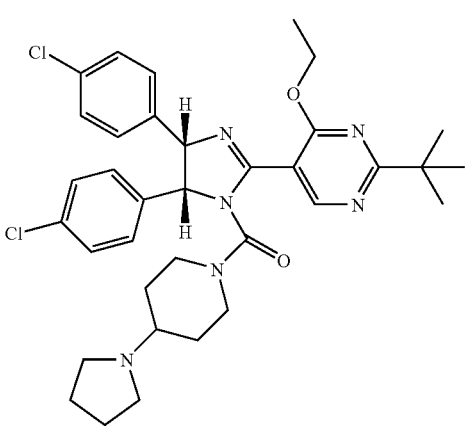

cis-4-[2-(2-tert-butyl-4-ethoxy-pyrimidin-5-yl)-4,5-bis-(4-chloro-phenyl)-4,5-dihydro-imidazole-1-carbonyl chloride (example 20) was reacted with 4-pyrrolidin-1-yl-piperidine (Aldrich) to give cis-[2-(2-tert-butyl-4-ethoxy-pyrimidin-5-yl)-4,5-bis-(4-chloro-phenyl)-4,5-dihydro-imidazol-1-yl]-(4-pyrrolidin-1-yl-piperidin-1-yl)-methanone in an analogous manner as described in example 1. HR-MS (ES, m/z) calculated for $C_{35}H_{42}N_6O_2Cl_2$ [(M+H)$^+$] 649.2819, observed 649.2822.

Example 26 cis-1-{4-[2-(2-tert-Butyl-4-ethoxy-pyrimidin-5-yl)-4,5-bis-(4-chloro-phenyl)-4,5-dihydro-imidazole-1-carbonyl]-Piperazin-1-yl}-ethanone

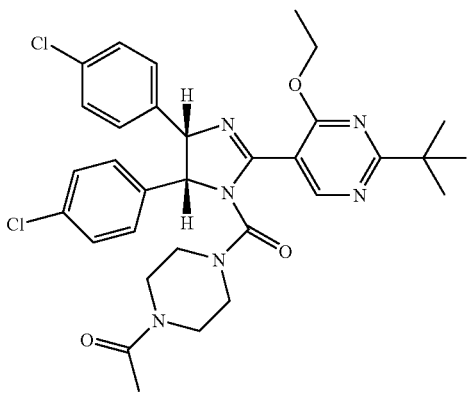

cis-4-[2-(2-tert-butyl-4-ethoxy-pyrimidin-5-yl)-4,5-bis-(4-chloro-phenyl)-4,5-dihydro-imidazole-1-carbonyl chloride (example 20) was reacted with 1-acetyl-piperazine (Aldrich) to give cis-1-{4-[2-(2-tert-butyl-4-ethoxy-pyrimidin-5-yl)-4,5-bis-(4-chloro-phenyl)-4,5-dihydro-imidazole-1-carbonyl]-piperazin-1-yl}-ethanone in an analogous manner as described in example 1. HR-MS (ES, m/z) calculated for $C_{32}H_{37}N_6O_3Cl_2$ [(M+H)$^+$] 623.2299, observed 623.2303.

Example 27 cis-[2-(2-tert-Butyl-4-ethoxy-pyrimidin-5-yl)-4,5-bis-(4-chloro-phenyl)-4,5-dihydro-imidazol-1-yl]-(4-methyl-piperazin-1-yl)-methanone

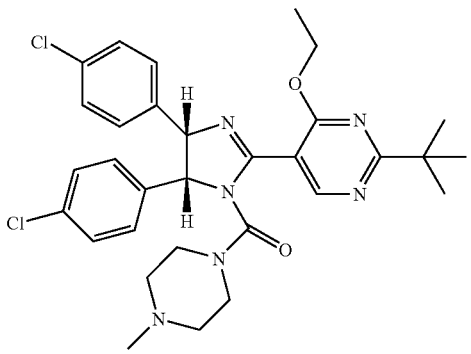

cis-4-[2-(2-tert-butyl-4-ethoxy-pyrimidin-5-yl)-4,5-bis-(4-chloro-phenyl)-4,5-dihydro-imidazole-1-carbonyl chloride (example 20) was reacted with 1-methyl-piperazine (Aldrich) to give cis-[2-(2-tert-butyl-4-ethoxy-pyrimidin-5-yl)-4,5-bis-(4-chloro-phenyl)-4,5-dihydro-imidazol-1-yl]-(4-methyl-piperazin-1-yl)-methanone in an analogous manner as described in example 1. HR-MS (ES, m/z) calculated for $C_{32}H_{37}N_6O_2Cl_2$ [(M+H)$^+$] 595.2350, observed 595.2351.

Example 28 cis-[2-(2-tert-Butyl-4-ethoxy-pyrimidin-5-yl)-4,5-bis-(4-chloro-phenyl)-4,5-dihydro-imidazol-1-yl]-[4-(3-methanesulfonyl-propyl)-piperazin-1-yl]-methanone

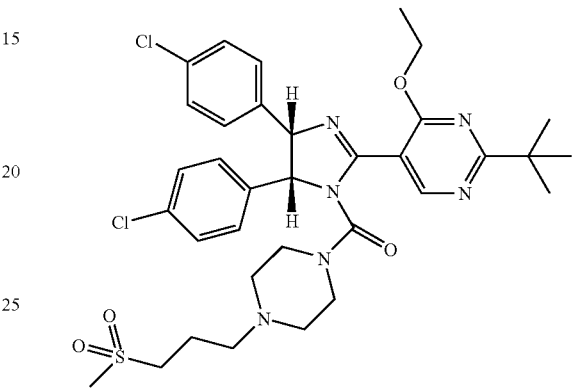

1-(3-Methanesulfonyl-propyl)-piperazine dihydrochloride was prepared from 1-tert-butyloxycarbonyl-piperazine and methanesulfonic acid 3-methanesulfonyl-propyl ester (prepared according to Baerlocher, F. J. et al. *Aust. J. Chem.* 1999, 52, 167-172) in an analogous manner as described for the preparation of N-(2-methoxy-1-methyl-ethyl)-2-piperazin-1-yl-acetamide dihydrochloride (example 40).

cis-4-[2-(2-tert-Butyl-4-ethoxy-pyrimidin-5-yl)-4,5-bis-(4-chloro-phenyl)-4,5-dihydro-imidazole-1-carbonyl chloride (example 20) was reacted with 1-(3-methanesulfonyl-propyl)-piperazine dihydrochloride to give cis-[2-(2-tert-butyl-4-ethoxy-pyrimidin-5-yl)-4,5-bis-(4-chloro-phenyl)-4,5-dihydro-imidazol-1-yl]-[4-(3-methanesulfonyl-propyl)-piperazin-1-yl]-methanone in an analogous manner as described in example 1. HR-MS (ES, m/z) calculated for $C_{34}H_{43}N_6O_4SCl_2$ [(M+H)$^+$] 701.2438, observed 701.2439.

Example 29 cis-[2-(2-tert-Butyl-4-ethoxy-pyrimidin-5-yl)-4,5-bis-(4-chloro-phenyl)-4,5-dihydro-imidazol-1-yl]-[4-(2-hydroxy-ethyl)-piperazin-1-yl]-methanone

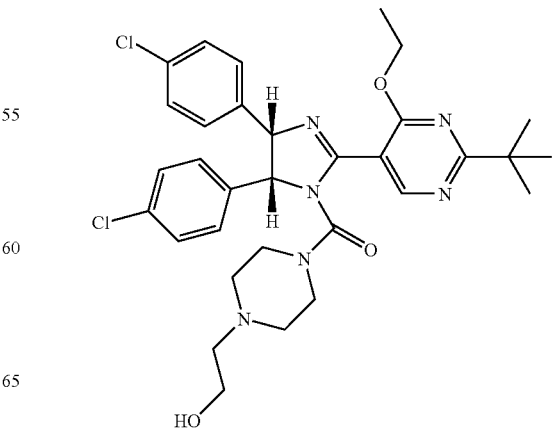

cis-4-[2-(2-tert-Butyl-4-ethoxy-pyrimidin-5-yl)-4,5-bis-(4-chloro-phenyl)-4,5-dihydro-imidazole-1-carbonyl chloride (example 20) was reacted with 2-piperazine-1-yl-ethanol (Aldrich) to give cis-[2-(2-tert-butyl-4-ethoxy-pyrimidin-5-yl)-4,5-bis-(4-chloro-phenyl)-4,5-dihydro-imidazol-1-yl]-[4-(2-hydroxy-ethyl)-piperazin-1-yl]-methanone in an analogous manner as described in example 1. HR-MS (ES, m/z) calculated for $C_{32}H_{39}N_6O_3Cl_2$ [(M+H)$^+$] 625.2455, observed 625.2457.

Example 30

2-{4-[(4S,5R)-2-(2-tert-Butyl-4-ethoxy-pyrimidin-5-yl)-4,5-bis-(4-chloro-phenyl)-4,5-dihydro-imidazole-1-carbonyl]-piperazin-1-yl}-1-morpholin-4-yl-ethanone Chiral

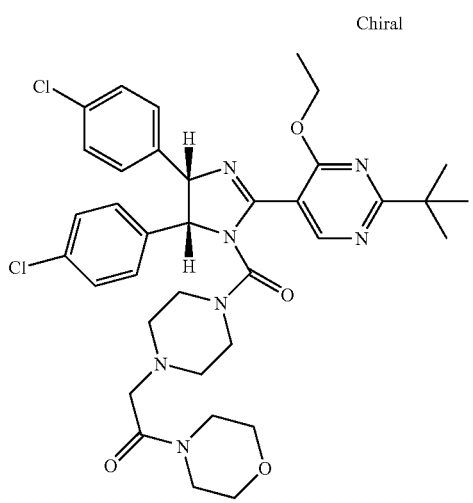

The enantiomers of cis-2-{4-[2-(2-tert-butyl-4-ethoxy-pyrimidin-5-yl)-4,5-bis-(4-chloro-phenyl)-4,5-dihydro-imidazole-1-carbonyl]-piperazin-1-yl}-1-morpholin-4-yl-ethanone (example 23) were separated by chiral chromatography using a ChiralPak OD column. Eluent: 60% ethanol in hexane. The first peak coming off the column is the desired enantiomer, 2-{4-[(4S,5R)-2-(2-tert-butyl-4-ethoxy-pyrimidin-5-yl)-4,5-bis-(4-chloro-phenyl)-4,5-dihydro-imidazole-1-carbonyl]-piperazin-1-yl}-1-morpholin-4-yl-ethanone. LR-MS: 708.0 [(M+H)$^+$]

Example 31

4-[(4S,5R)-2-(2-tert-Butyl-4-ethoxy-pyrimidin-5-yl)-4,5-bis-(4-chloro-phenyl)-4,5-dihydro-imidazole-1-carbonyl]-piperazin-2-one Chiral

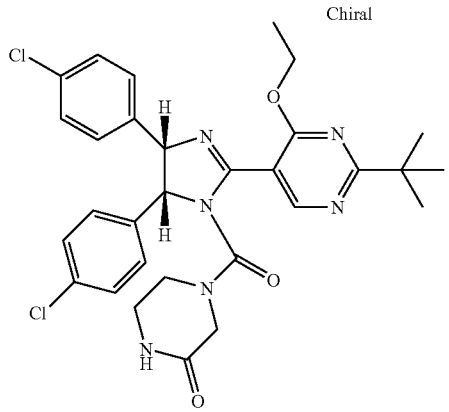

The enantiomers of cis-4-[2-(2-tert-butyl-4-ethoxy-pyrimidin-5-yl)-4,5-bis-(4-chloro-phenyl)-4,5-dihydro-imidazole-1-carbonyl]-piperazin-2-one (example 20) were separated by chiral chromatography using a ChiralPak OD column. Eluent: 60% ethanol in hexane. The first peak coming off the column is the desired enantiomer, 4-[(4S,5R)-2-(2-tert-butyl-4-ethoxy-pyrimidin-5-yl)-4,5-bis-(4-chloro-phenyl)-4,5-dihydro-imidazole-1-carbonyl]-piperazin-2-one. LR-MS: 595.2 [(M+H)$^+$]

Example 32 cis-4-[4,5-Bis-(4-chloro-phenyl)-2-(4,6-diethoxy-pyridin-3-yl)-4,5-dihydro-imidazole-1-carbonyl]-piperazin-2-one hydrochloride

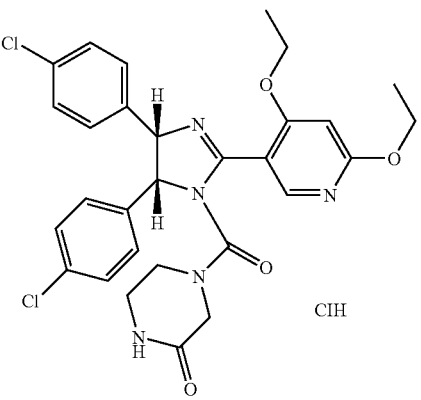

2,4-Diethoxy-5-carbethoxypyridine (prepared from 2,4-dichloro-5-carbethoxypyridine and sodium ethoxy using the procedure described by Nesnow, S. et al. *J. Med. Chem.* 1973, 16, 524) was reacted with meso-1,2-bis-(4-chlorophenyl)-ethane-1,2-diamine in an analogous manner as described in example 1 to give cis-4-[4,5-bis-(4-chloro-phenyl)-2-(4,6-diethoxy-pyridin-3-yl)-4,5-dihydro-1H-imidazole.

Using the procedure as described in example 1, cis-4-[4,5-bis-(4-chloro-phenyl)-2-(4,6-diethoxy-pyridin-3-yl)-4,5-dihydro-1H-imidazole was reacted with phosgene to give cis-4-[4,5-bis-(4-chloro-phenyl)-2-(4,6-diethoxy-pyridin-3-yl)-4,5-dihydro-imidazole-1-carbonyl chloride. The carbonyl chloride was then coupled with 2-piperazinone (Alfa) to give cis-4-[4,5-bis-(4-chloro-phenyl)-2-(4,6-diethoxy-pyridin-3-yl)-4,5-dihydro-imidazole-1-carbonyl]-piperazin-2-one hydrochloride.

Example 33
cis-[4,5-Bis-(4-chloro-phenyl)-2-(4,6-diethoxy-pyridin-3-yl)-4,5-dihydro-imidazol-1-yl]-[4-(2-hydroxy-ethyl)-piperazin-1-yl]-methanone hydrochloride

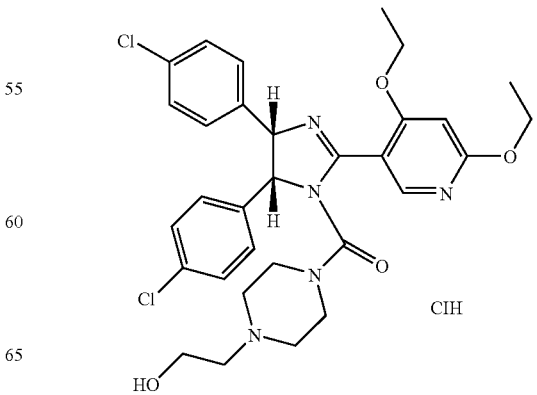

cis-4-[4,5-Bis-(4-chloro-phenyl)-2-(4,6-diethoxy-pyridin-3-yl)-4,5-dihydro-imidazole-1-carbonyl chloride (example 32) was reacted with 2-piperazine-1-yl-ethanol (Aldrich) to give cis-[4,5-bis-(4-chloro-phenyl)-2-(4,6-diethoxy-pyridin-3-yl)-4,5-dihydro-imidazol-1-yl]-[4-(2-hydroxy-ethyl)-piperazin-1-yl]-methanone hydrochloride in an analogous manner as described in example 1.

Example 34

2-{4-[(4S,5R)-4,5-Bis-(4-chloro-phenyl)-2-(3-ethoxy-thiophen-2-yl)-4,5-dihydro-imidazole-1-carbonyl]-piperazin-1-yl}-N-tert-butyl-acetamide

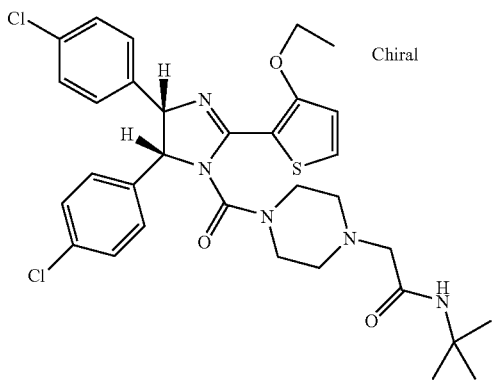

N-tert-butyl-2-piperazin-1-yl-acetamide dihydrochloride was prepared from 1-tert-butyloxycarbonyl-piperazine, chloroacetylchloride and N-tert-butylamine in an analogous manner as described for the preparation of N-(2-methoxy-1-methyl-ethyl)-2-piperazin-1-yl-acetamide dihydrochloride (example 40).

3-Ethoxy-thiophene-2-carboxylic acid ethyl ester (prepared from 3-hydroxy-thiophene-2-carboxylic acid) was reacted with meso-1,2-bis-(4-chlorophenyl)-ethane-1,2-diamine in an analogous manner as described in example 1 to give cis-4,5-bis-(4-chloro-phenyl)-2-(3-ethoxy-thiophen-2-yl)-4,5-dihydro-1H-imidazole.

Using the procedure as described in example 1, cis-4,5-bis-(4-chloro-phenyl)-2-(3-ethoxy-thiophen-2-yl)-4,5-dihydro-1H-imidazole was reacted with phosgene to give cis-4,5-bis-(4-chloro-phenyl)-2-(3-ethoxy-thiophen-2-yl)-4,5-dihydro-imidazole-1-carbonyl chloride. The enantiomers of cis-4,5-bis-(4-chloro-phenyl)-2-(3-ethoxy-thiophen-2-yl)-4,5-dihydro-imidazole-1-carbonyl chloride were separated by chiral chromatography using a Modcol spring column (50 mm×70 cm) packed with R,R-Whelk-O1 spherical Kromasil silica gel (Regis Technologies, eluent: 30% methylene chloride in hexane, flowrate: 85 mL/min) to give the desired 2-{4-[(4S,5R)-4,5-bis-(4-chloro-phenyl)-2-(3-ethoxy-thiophen-2-yl)-4,5-dihydro-imidazole-1-carbonyl chloride.

2-{4-[(4S,5R)-4,5-Bis-(4-chloro-phenyl)-2-(3-ethoxy-thiophen-2-yl)-4,5-dihydro-imidazole-1-carbonyl chloride was reacted with N-tert-butyl-2-piperazin-1-yl-acetamide dihydrochloride to give 2-{4-[(4S,5R)-4,5-bis-(4-chloro-phenyl)-2-(3-ethoxy-thiophen-2-yl)-4,5-dihydro-imidazole-1-carbonyl]-piperazin-1-yl}-N-tert-butyl-acetamide in an analogous manner as described in example 1. LR-MS: 642.3 [(M+H)$^+$]

Example 35

2-{4-[(4S,5R)-4,5-Bis-(4-chloro-phenyl)-2-(3-ethoxy-thiophen-2-yl)-4,5-dihydro-imidazole-1-carbonyl]-piperazin-1-yl}-acetamide

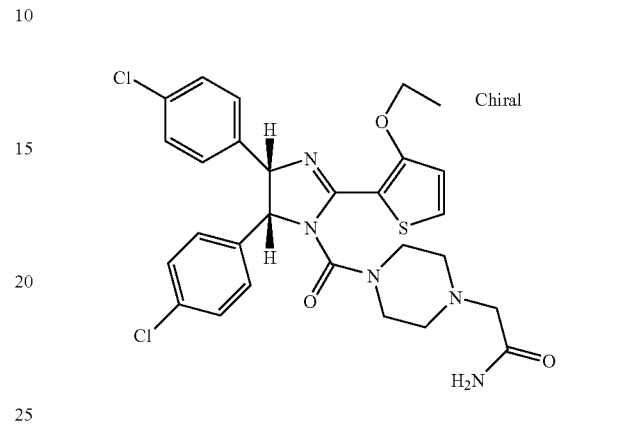

2-{4-[(4S,5R)-4,5-Bis-(4-chloro-phenyl)-2-(3-ethoxy-thiophen-2-yl)-4,5-dihydro-imidazole-1-carbonyl chloride (example 34) was reacted with 2-piperazin-1-yl-acetamide hydrochloride (Matrix) to give 2-{4-[(4S,5R)-4,5-bis-(4-chloro-phenyl)-2-(3-ethoxy-thiophen-2-yl)-4,5-dihydro-imidazole-1-carbonyl]-piperazin-1-yl}-acetamide in an analogous manner as described in example 1. LR-MS: 586.2 [(M+H)$^+$]

Example 36

2-{4-[(4S,5R)-4,5-Bis-(4-chloro-phenyl)-2-(3-ethoxy-thiophen-2-yl)-4,5-dihydro-imidazole-1-carbonyl]-piperazin-1-yl}-N,N-bis-(2-methoxy-ethyl)-acetamide

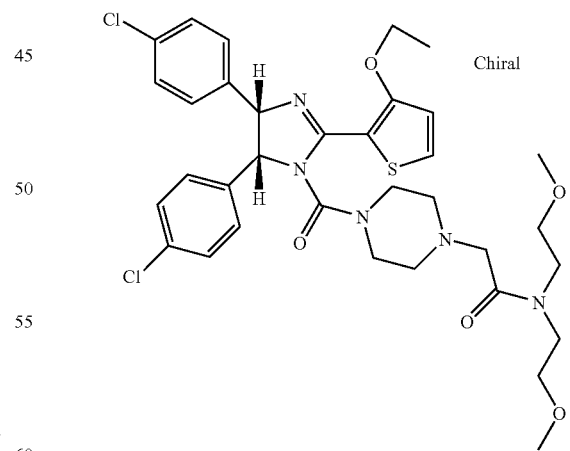

N,N-Bis-(2-methoxy-ethyl)-2-piperazin-1-yl-acetamide dihydrochloride was prepared from 1-tert-butyloxycarbonyl-piperazine, chloroacetylchloride and N,N-bis-(2-methoxy-ethyl)amine in an analogous manner as described for the preparation of N-(2-methoxy-1-methyl-ethyl)-2-piperazin-1-yl-acetamide dihydrochloride (example 40).

2-{4-[(4S,5R)-4,5-Bis-(4-chloro-phenyl)-2-(3-ethoxy-thiophen-2-yl)-4,5-dihydro-imidazole-1-carbonyl chloride (example 34) was reacted with N,N-bis-(2-methoxy-ethyl)-2-piperazin-1-yl-acetamide dihydrochloride to give 2-(4-[(4S,5R)-4,5-bis-(4-chloro-phenyl)-2-(3-ethoxy-thiophen-2-yl)-4,5-dihydro-imidazole-1-carbonyl]-piperazin-1-yl}-N,N-bis-(2-methoxy-ethyl)-acetamide in an analogous manner as described in example 1. LR-MS: 702.3 [(M+H)⁺]

Example 37

2-{4-[(4S,5R)-4,5-Bis-(4-chloro-phenyl)-2-(3-ethoxy-thiophen-2-yl)-4,5-dihydro-imidazole-1-carbonyl]-piperazin-1-yl}-N-methoxy-N-methyl-acetamide

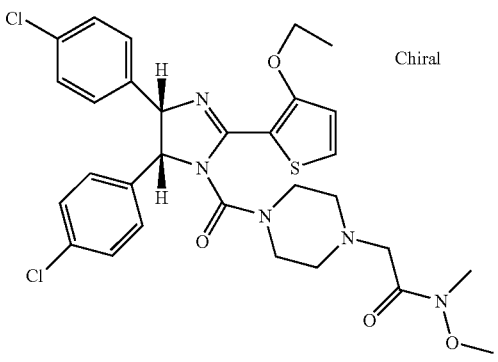

N-Methoxy-N-methyl-2-piperazin-1-yl-acetamide dihydrochloride was prepared from 1-tert-butyloxycarbonyl-piperazine, chloroacetylchloride and N-methoxy-N-methylamine in an analogous manner as described for the preparation of N-(2-methoxy-1-methyl-ethyl)-2-piperazin-1-yl-acetamide dihydrochloride (example 40).
2-{4-[(4S,5R)-4,5-Bis-(4-chloro-phenyl)-2-(3-ethoxy-thiophen-2-yl)-4,5-dihydro-imidazole-1-carbonyl chloride (example 34) was reacted with N-methoxy-N-methyl-2-piperazin-1-yl-acetamide dihydrochloride to give 2-{4-[(4S,5R)-4,5-bis-(4-chloro-phenyl)-2-(3-ethoxy-thiophen-2-yl)-4,5-dihydro-imidazole-1-carbonyl]-piperazin-1-yl}-N-methoxy-N-methyl-acetamide in an analogous manner as described in example 1. LR-MS: 630.3 [(M+H)⁺].

Example 38

2-{4-[(4S,5R)-4,5-Bis-(4-chloro-phenyl)-2-(3-ethoxy-thiophen-2-yl)-4,5-dihydro-imidazole-1-carbonyl]-piperazin-1-yl}-N-isopropyl-N-methyl-acetamide

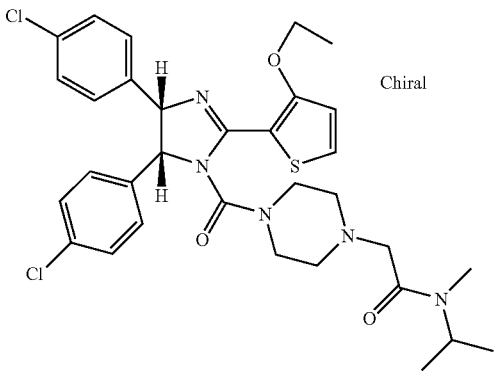

N-Isopropyl-N-methyl-2-piperazin-1-yl-acetamide dihydrochloride was prepared from 1-tert-butyloxycarbonyl-piperazine, chloroacetylchloride and N-isopropyl-N-methylamine in an analogous manner as described for the preparation of N-(2-methoxy-1-methyl-ethyl)-2-piperazin-1-yl-acetamide dihydrochloride (example 40).

2-{4-[(4S,5R)-4,5-Bis-(4-chloro-phenyl)-2-(3-ethoxy-thiophen-2-yl)-4,5-dihydro-imidazole-1-carbonyl chloride (example 34) was reacted with N-isopropyl-N-methyl-2-piperazin-1-yl-acetamide dihydrochloride to give 2-{4-[(4S,5R)-4,5-bis-(4-chloro-phenyl)-2-(3-ethoxy-thiophen-2-yl)-4,5-dihydro-imidazole-1-carbonyl]-piperazin-1-yl}-N-isopropyl-N-methyl-acetamide in an analogous manner as described in example 1. LR-MS: 642.3 [(M+H)⁺].

Example 39

2-{4-[(4S,5R)-4,5-Bis-(4-chloro-phenyl)-2-(3-ethoxy-thiophen-2-yl)-4,5-dihydro-imidazole-1-carbonyl]-piperazin-1-yl}-N-(2-cyano-ethyl)-N-methyl-acetamide

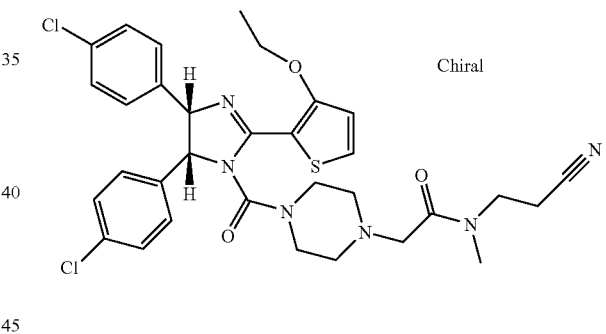

N-(2-Cyano-ethyl)-N-methyl-2-piperazin-1-yl-acetamide dihydrochloride was prepared from 1-tert-butyloxycarbonyl-piperazine, chloroacetylchloride and N-(2-cyanoethyl)-N-methylamine in an analogous manner as described for the preparation of N-(2-methoxy-1-methyl-ethyl)-2-piperazin-1-yl-acetamide dihydrochloride (example 40).

2-{4-[(4S,5R)-4,5-Bis-(4-chloro-phenyl)-2-(3-ethoxy-thiophen-2-yl)-4,5-dihydro-imidazole-1-carbonyl chloride (example 34) was reacted with N-(2-cyano-ethyl)-N-methyl-2-piperazin-1-yl-acetamide dihydrochloride to give 2-{4-[(4S,5R)-4,5-bis-(4-chloro-phenyl)-2-(3-ethoxy-thiophen-2-yl)-4,5-dihydro-imidazole-1-carbonyl]-piperazin-1-yl}-N-(2-cyano-ethyl)-N-methyl-acetamide in an analogous manner as described in example 1. LR-MS: 653.2 [(M+H)⁺].

Example 40 cis-2-{4-[4,5-Bis-(4-chloro-Phenyl)-2-(3-ethoxy-thiophen-2-yl)-4,5-dihydro-imidazole-1-carbonyl]-piperazin-1-yl}-N-(2-methoxy-1-methyl-ethyl)-acetamide

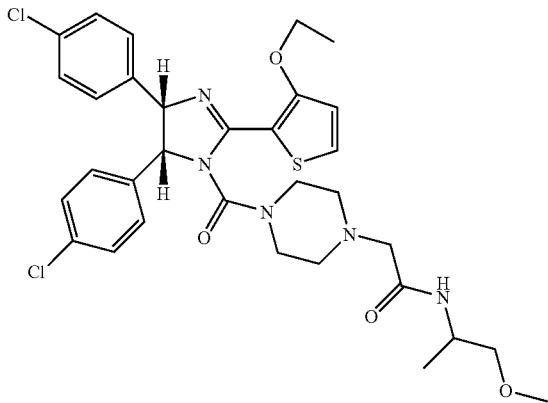

2-Methoxy-1-methyl-ethylamine (15 mmol, 1.15 eq) and diisopropylethylamine (17 mmol, 1.3 eq) were diluted with methylene chloride to give a total volume of 8 mL. The amine solution was added in a portion-wise fashion via a syringe to a solution of chloroacetyl chloride (13 mmol) in methylene chloride (10 mL) cooled to approximately −40° C. in a sealed 40 mL vial. The reaction mixture was stirred for 1 h at reduced temperature. The solution was then made acidic with 1N hydrochloric acid and then diluted with 10 mL of methylene chloride. The vial was agitated and centrifuged. The organic layer was transferred to 40 mL vials and concentrated in vacuo. The residue (1.69 g, 10.21 mmol) was diluted with 10 mL of dimethylformamide. Piperazine-1-carboxylic acid tert-butyl ester (8.67 mmol, 0.85 eq) and diisopropylethylamine (13.27 mmol, 1.3 eq) were added. The reaction mixture was shaken at 65° C. overnight and concentrated in vacuo. The crude residue was dissolved in 10 mL of dioxane and 10 mL of 4M hydrochloric acid in dioxane.

The solution was shaken overnight at room temperature then centrifuged. The supernatant was removed, and the remaining solids were shaken with hexane then centrifuged. The supernatant was removed, and the solids was collected and dried in vacuo to give N-(2-methoxy-1-methylethyl)-2-piperazin-1-yl-acetamide dihydrochloride. LR-MS: 216.4 [(M+H)$^+$].

2-{4-[(4S,5R)-4,5-Bis-(4-chloro-phenyl)-2-(3-ethoxy-thiophen-2-yl)-4,5-dihydro-imidazole-1-carbonyl chloride (example 34) was reacted with N-(2-methoxy-1-methyl-ethyl)-2-piperazin-1-yl-acetamide dihydrochloride to give cis-2-{4-[4,5-bis-(4-chloro-phenyl)-2-(3-ethoxy-thiophen-2-yl)-4,5-dihydro-imidazole-1-carbonyl]-piperazin-1-yl}-N-(2-methoxy-1-methyl-ethyl)-acetamide in an analogous manner as described in example 1. LR-MS: 658.2 [(M+H)$^+$].

Example 41

[(4S,5R)-4,5-Bis-(4-chloro-phenyl)-2-(3-ethoxy-thiophen-2-yl)-4,5-dihydro-imidazol-1-yl]-[4-(3,5-dimethyl-isoxazole-4-carbonyl)-piperazin-1-yl]-methanone

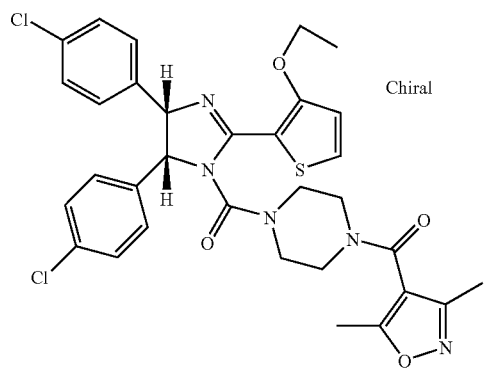

A solution of 1-tert-butyloxycarbonyl-piperazine (4.581 mmol, 0.9 eq) and diisopropylethylamine (5.09 mmol, 1.0 eq) in methylene chloride (5 mL) was added to a 40 mL vial. 3,5-Dimethyl-isoxazole-4-carbonyl chloride (5.09 mmol, 1.0 eq) was added to the vial and the reaction was shaken overnight at room temperature. When the reaction was complete, it was diluted with methylene chloride (5 mL) and washed with 4 mL of 1N hydrochloric acid followed by 4 mL of 10% potassium carbonate. The organic layer was concentrated in vacuo. The crude residue was dissolved in 5 mL of dioxane and 5 mL of 4M hydrochloric acid in dioxane. The reaction mixture was shaken overnight at room temperature then centrifuged. The supernatant was removed and the remaining solid was shaken with hexane then centrifuged. The supernatant was removed, and the solids were collected and dried in vacuo to give (3,5-dimethyl-isoxazol-4-yl)-piperazin-1-yl-methanone. LR-MS: 210.2 [(M+H)$^+$].

2-{4-[(4S,5R)-4,5-Bis-(4-chloro-phenyl)-2-(3-ethoxy-thiophen-2-yl)-4,5-dihydro-imidazole-1-carbonyl chloride (example 34) was reacted with (3,5-dimethyl-isoxazol-4-yl)-piperazin-1-yl-methanone to give [(4S,5R)-4,5-bis-(4-chloro-phenyl)-2-(3-ethoxy-thiophen-2-yl)-4,5-dihydro-imidazol-1-yl]-[4-(3,5-dimethyl-isoxazole-4-carbonyl)-piperazin-1-yl]-methanone in an analogous manner as described in example 1. LR-MS: 652.2 [(M+H)$^+$].

Example 42

[(4S,5R)-4,5-Bis-(4-chloro-phenyl)-2-(3-ethoxy-thiophen-2-yl)-4,5-dihydro-imidazol-1-yl]-(4-ethanesulfonyl-piperazin-1-yl)-methanone

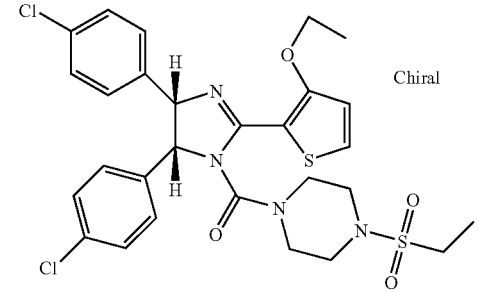

Ethanesulfonyl-piperazine was prepared from 1-tert-butyloxycarbonyl-piperazine and ethylsulfonyl chloride in an analogous manner as described for the preparation of (3,5-dimethyl-isoxazol-4-yl)-piperazin-1-yl-methanone in example 41.

2-{4-[(4S,5R)-4,5-Bis-(4-chloro-phenyl)-2-(3-ethoxy-thiophen-2-yl)-4,5-dihydro-imidazole-1-carbonyl chloride (example 34) was reacted with 1-ethanesulfonyl-piperazine to give [(4S,5R)-4,5-bis-(4-chloro-phenyl)-2-(3-ethoxy-thiophen-2-yl)-4,5-dihydro-imidazol-1-yl]-(4-ethanesulfonyl-piperazin-1-yl)-methanone in an analogous manner as described in example 1. LR-MS: 621.2 [(M+H)+]

Example 43

N-(2-{4-[(4S,5R)-4,5-Bis-(4-chloro-phenyl)-2-(3-ethoxy-thiophen-2-yl)-4,5-dihydro-imidazole-1-carbonyl]-piperazin-1-yl}-ethyl)-methanesulfonamide

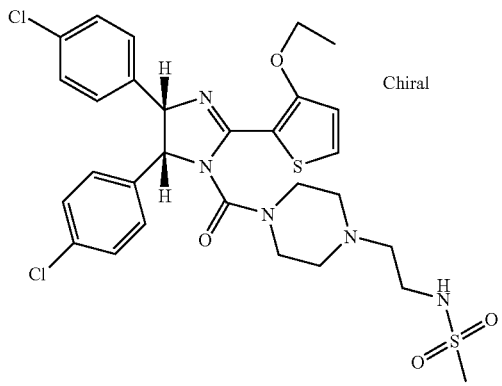

Methanesulfonyl chloride (0.7 mL, 9.0 mmol) was added to a cooled solution of 4-(2-amino-ethyl)-piperazine-1-carboxylic acid tert-butyl ester (1.33 g, 5.8 mmol) in pyridine (25.0 mL). The reaction was stirred for 12 h and partitioned between partitioned between aqueous sodium bicarbonate and methylene chloride. The organic phase was washed with 1M hydrochloric acid, aqueous sodium bicarbonate, brine, dried over anhydrous magnesium sulfate and concentrated. Purification of the crude residue by flash chromatography over silica gel using 0-5% methanol in methylene chloride gave 4-(2-methanesulfonylamino-ethyl)-piperazine-1-carboxylic acid tert-butyl ester (0.70 g, 70%).

To a cooled solution of 4-(2-methanesulfonylamino-ethyl)-piperazine-1-carboxylic acid tert-butyl ester (0.64 g, 0.2 mmol) in dioxane (20 mL) was added hydrochloric acid (4M in dioxane, 10 mL) and the reaction was stirred at room temperature for 12 h and concentrated to give N-(2-methanosulfonylethyl)-piperazine dihydrochloride as a white solid (0.55 g, 95%).

2-{4-[(4S,5R)-4,5-Bis-(4-chloro-phenyl)-2-(3-ethoxy-thiophen-2-yl)-4,5-dihydro-imidazole-1-carbonyl chloride (example 34) was reacted with N-(2-methanosulfonylethyl)-piperazine dihydrochloride to give N-(2-{4-[(4S,5R)-4,5-bis-(4-chloro-phenyl)-2-(3-ethoxy-thiophen-2-yl)-4,5-dihydro-imidazole-1-carbonyl]-piperazin-1-yl}-ethyl)-methanesulfonamide in an analogous manner as described in example 1. LR-MS: 650.1 [(M+H)+].

Example 44

[(4S,5R)-4,5-Bis-(4-chloro-Phenyl)-2-(3-ethoxy-thiophen-2-yl)-4,5-dihydro-imidazol-1-yl]-[4-(3-methanesulfonyl-propyl)-piperazin-1-yl]-methanone

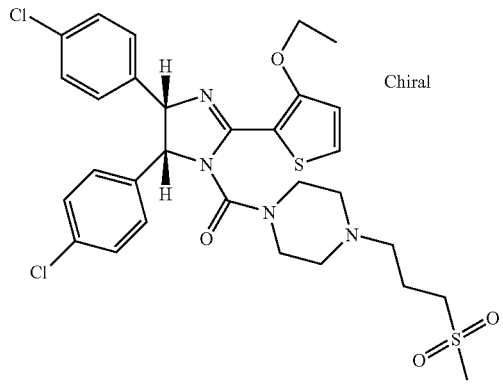

2-{4-[(4S,5R)-4,5-Bis-(4-chloro-phenyl)-2-(3-ethoxy-thiophen-2-yl)-4,5-dihydro-imidazole-1-carbonyl chloride (example 34) was reacted with 1-(3-methanesulfonyl-propyl)-piperazine dihydrochloride (example 28) to give [(4S,5R)-4,5-bis-(4-chloro-phenyl)-2-(3-ethoxy-thiophen-2-yl)-4,5-dihydro-imidazol-1-yl]-[4-(3-methanesulfonyl-propyl)-piperazin-1-yl]-methanone in an analogous manner as described in example 1. LR-MS: 649.2 [(M+H)+].

Example 45

[(4S,5R)-4,5-Bis-(4-chloro-phenyl)-2-(3-ethoxy-thiophen-2-yl)-4,5-dihydro-imidazol-1-yl]-[4-(2-methanesulfonyl-ethyl)-piperazin-1-yl]-methanone

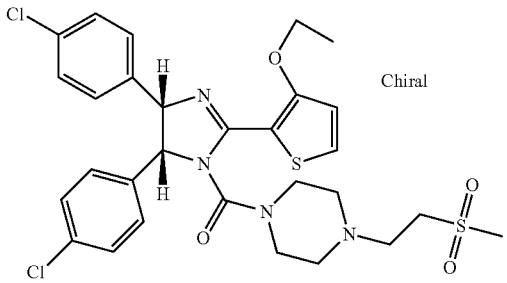

2-{4-[(4S,5R)-4,5-Bis-(4-chloro-phenyl)-2-(3-ethoxy-thiophen-2-yl)-4,5-dihydro-imidazole-1-carbonyl chloride was reacted with 1-(2-methanesulfonylethyl)piperazine dihydrochloride (example 3) to give [(4S,5R)-4,5-bis-(4-chloro-phenyl)-2-(3-ethoxy-thiophen-2-yl)-4,5-dihydro-imidazol-1-yl]-[4-(2-methanesulfonyl-ethyl)-piperazin-1-yl]-methanone in an analogous manner as described in example 1. LR-MS: 635.1 [(M+H)+].

Example 46

2-{4-[(4S,5R)-4,5-Bis-(4-chloro-phenyl)-2-(3-ethoxy-thiophen-2-yl)-4,5-dihydro-imidazole-1-carbonyl]-piperazin-1-yl}-1-morpholin-4-yl-ethanone

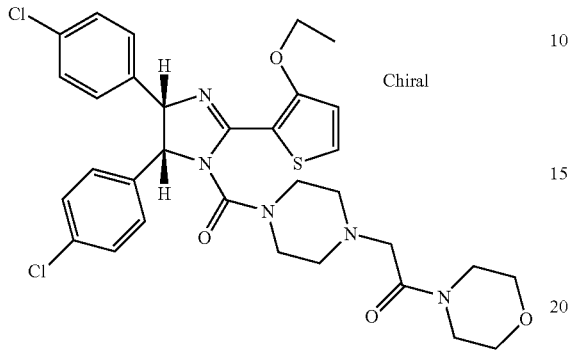

2-{4-[(4S,5R)-4,5-Bis-(4-chloro-phenyl)-2-(3-ethoxy-thiophen-2-yl)-4,5-dihydro-imidazole-1-carbonyl chloride (example 28) was reacted with 1-morpholin-4-yl-2-piperazin-1-yl-ethanone (Oakwood Products) to give 2-{4-[(4S,5R)-4,5-bis-(4-chloro-phenyl)-2-(3-ethoxy-thiophen-2-yl)-4,5-dihydro-imidazole-1-carbonyl]-piperazin-1-yl}-1-morpholin-4-yl-ethanone in an analogous manner as described in example 1. LR-MS: 656.3 $[(M+H)^+]$.

Example 47

In Vitro Activity Assay

The ability of the compounds to inhibit the interaction between p53 and MDM2 proteins was measured by an HTRF (homogeneous time-resolved fluorescence) assay in which recombinant GST-tagged MDM2 binds to a peptide that resembles the MDM2-interacting region of p53 (Lane et al.). Binding of GST-MDM2 protein and p53-peptide (biotinylated on its N-terminal end) is registered by the FRET (fluorescence resonance energy transfer) between Europium (Eu)-labeled anti-GST antibody and streptavidin-conjugated Allophycocyanin (APC).

Test is performed in black flat-bottom 384-well plates (Costar) in a total volume of 40 uL containing: 90 nM biotinylate peptide, 160 ng/mL GST-MDM2, 20 nM streptavidin-APC (PerkinElmerWallac), 2 nM Eu-labeled anti-GST-antibody (PerkinElmerWallac), 0.2% bovine serum albumin (BSA), 1 mM dithiothreitol (DTT) and 20 mM Tris-borate saline (TBS) buffer as follows: Add 10 uL of GST-MDM2 (640 ng/mL working solution) in reaction buffer to each well. Add 10 uL diluted compounds (1:5 dilution in reaction buffer) to each well, mix by shaking. Add 20 uL biotinylated p53 peptide (180 nM working solution) in reaction buffer to each well and mix on shaker. Incubate at 37° C. for 1 h. Add 20 uL streptavidin-APC and Eu-anti-GST antibody mixture (6 nM Eu-anti-GST and 60 nM streptavidin-APC working solution) in TBS buffer with 0.2% BSA, shake at room temperature for 30 minutes and read using a TRF-capable plate reader at 665 and 615 nm (Victor 5, Perkin ElmerWallac). If not specified, the reagents were purchased from Sigma Chemical Co.

$IC_{50}$s showing biological activity that applies to compounds of the subject matter of this invention ranges from about 0.030 uM to about 7 uM. Specific data for some examples are as follows:

| Example | $IC_{50}$ (μM) |
|---|---|
| 6 | 2.890 |
| 17 | 0.677 |
| 20 | 0.046 |
| 34 | 0.110 |
| 36 | 0.054 |

What is claimed:
1. The compound of formula I

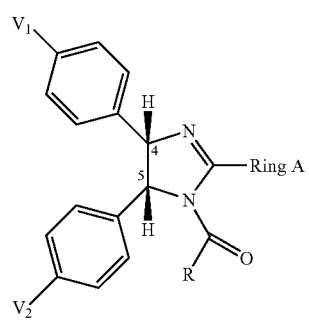

and the pharmaceutically acceptable salts and esters thereof, wherein

Ring A is:

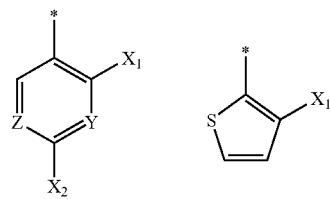

$X_1$ is selected from the group consisting of
  lower alkoxy, and
  lower alkoxy substituted by trifluoromethyl or fluorine;
$X_2$ is selected from the group consisting of
  hydrogen,
  thioalkyl,
  lower alkyl,
  lower alkoxy,
  morpholino, and
  $-NX_3X_4$;
$X_3$ and $X_4$ are independently selected from the group consisting of
  hydrogen,
  lower alkyl,
  lower alkyl substituted by lower alkoxy or cyano, and
  lower alkoxy;
Y and Z are independently selected from the group consisting of:
  carbon, and nitrogen;

V₁ and V₂ are independently selected from the group consisting of
halogen,
cyano, and
acetylene;
R is selected from the group consisting of
piperidinyl substituted by five or six membered heterocycle,
piperidinyl substituted by —NX₃X₄, and

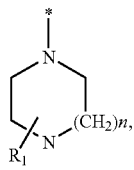

wherein
n=1 or 2,
R₁ can be one or more substituents selected from the group consisting of
hydrogen,
oxo,
lower alkyl substituted by R₂,
—C(O)R₃, and
—SO₂-lower alkyl;
R₂ is selected from the group consisting of
hydroxy,
lower alkoxy,
trifluoromethyl,
-cyano,
—NH—SO₂-lower alkyl,
—NH—C(O)-lower alkyl,
—C(O)-lower alkyl,
—C(O)R₄,
—C(O)—NX₃X₄,
—SO₂-lower alkyl,
—SO₂—NX₃X₄,
R₃ is selected from the group consisting of
five membered heterocycle,
lower alkyl,
lower alkoxy, and
lower alkyl substituted by lower alkoxy and
R₄ is selected from the group consisting of
hydroxy,
lower alkoxy,
morpholino, and
—NX₃X₄
with the proviso that at least one of Y and Z above is nitrogen.

2. The compound of claim 1 wherein the two hydrogen of the imidazoline ring are in the cis configuration to each other.

3. The compound of claim 1 wherein V₁ and V₂ are selected from —Cl or —Br.

4. The compound of claim 3 wherein X₁ is selected from ethoxy, isopropoxy, —OCH₂CF₃ or —OCH₂CH₂F.

5. The compound of claim 4 wherein X₂ is methyl, ethyl, isopropyl, tert-butyl, methoxy, ethoxy, thiomethyl, morpholino and —NX₃X₄.

6. The compound of claim 5 wherein R is piperazinyl substituted by oxo or lower alkyl substituted by R₂ wherein R₂ is SO₂-lower alkyl or —C(O)R₄.

7. A compound of claim 1 selected from the group consisting of
cis-4-[(4,5-Bis-(4-chloro-phenyl)-2-(2-ethoxy-pyridin-3-yl)-4,5-dihydro-imidazole-1-carbonyl]-piperazin-2-one,
cis-2-{4-[4,5-Bis-(4-chloro-phenyl)-2-(2-ethoxy-pyridin-3-yl)-4,5-dihydro-imidazole-1-carbonyl]-piperazin-1-yl}-N,N-dimethyl-acetamide,
cis-[4,5-Bis-(4-chloro-phenyl)-2-(2-ethoxy-pyridin-3-yl)-4,5-dihydro-imidazol-1-yl]-[4-(2-methanesulfonyl-ethyl)-piperazin-1-yl]-methanone,
cis-2-{4-[4,5-Bis-(4-chloro-phenyl)-2-(2-ethoxy-pyridin-3-yl)-4,5-dihydro-imidazole-1-carbonyl]-piperazin-1-yl}-1-morpholin-4-yl-ethanone,
cis-4-[4,5-Bis-(4-chloro-phenyl)-2-(4-ethoxy-2-trifluoromethyl-pyrimidin-5-yl)-4,5-dihydro-imidazole-1-carbonyl]-piperazin-2-one,
cis-[4,5-Bis-(4-chloro-phenyl)-2-(4-ethoxy-2-trifluoromethyl-pyrimidin-5-yl)-4,5-dihydro-imidazol-1-yl]-[4-(2-methanesulfonyl-ethyl)-piperazin-1-yl]-methanone,
cis-2-{4-[4,5-Bis-(4-chloro-phenyl)-2-(4-ethoxy-2-trifluoromethyl-pyrimidin-5-yl)-4,5-dihydro-imidazole-1-carbonyl]-piperazin-1-yl}-1-morpholin-4-yl-ethanone,
cis-4-[4,5-Bis-(4-chloro-phenyl)-2-(2,4-diethoxy-pyrimidin-5-yl)-4,5-dihydro-imidazole-1-carbonyl]-piperazin-2-one,
cis-2-{4-[4,5-Bis-(4-chloro-phenyl)-2-(2,4-diethoxy-pyrimidin-5-yl)-4,5-dihydro-imidazole-1-carbonyl]-piperazin-1-yl}-N,N-dimethyl-acetamide,
cis-[4,5-Bis-(4-chloro-phenyl)-2-(2,4-diethoxy-pyrimidin-5-yl)-4,5-dihydro-imidazol-1-yl]-[4-(2-methanesulfonyl-ethyl)-piperazin-1-yl]-methanone,
cis-2-{4-[4,5-Bis-(4-chloro-phenyl)-2-(2,4-diethoxy-pyrimidin-5-yl)-4,5-dihydro-imidazole-1-carbonyl]-piperazin-1-yl}-1-morpholin-4-yl-ethanone,
cis-4-[4,5-Bis-(4-chloro-phenyl)-2-(4-ethoxy-2-methylsulfanyl-pyrimidin-5-yl)-4,5-dihydro-imidazole-1-carbonyl]-piperazin-2-one and
cis-2-{4-[4,5-Bis-(4-chloro-phenyl)-2-(4-ethoxy-2-methylsulfanyl-pyrimidin-5-yl)-4,5-dihydro-imidazole-1-carbonyl]-piperazin-1-yl}-N,N-dimethyl-acetamide.

8. A compound of claim 1 selected from the group consisting of
cis-[4,5-Bis-(4-chloro-phenyl)-2-(4-ethoxy-2-methylsulfanyl-pyrimidin-5-yl)-4,5-dihydro-imidazol-1-yl]-[4-(2-methanesulfonyl-ethyl)-piperazin-1-yl]-methanone,
cis-2-{4-[4,5-Bis-(4-chloro-phenyl)-2-(4-ethoxy-2-methylsulfanyl-pyrimidin-5-yl)-4,5-dihydro-imidazole-1-carbonyl]-piperazin-1-yl}-1-morpholin-4-yl-ethanone,
cis-4-[4,5-Bis-(4-chloro-phenyl)-2-(4-ethoxy-2-methyl-pyrimidin-5-yl)-4,5-dihydro-imidazole-1-carbonyl]-piperazin-2-one,
cis-2-{4-[4,5-Bis-(4-chloro-phenyl)-2-(4-ethoxy-2-methyl-pyrimidin-5-yl)-4,5-dihydro-imidazole-1-carbonyl]-piperazin-1-yl}-N,N-dimethyl-acetamide,
cis-[4,5-Bis-(4-chloro-phenyl)-2-(4-ethoxy-2-methyl-pyrimidin-5-yl)-4,5-dihydro-imidazol-1-yl]-[4-(2-methanesulfonyl-ethyl)-piperazin-1-yl]-methanone,
cis-2-{4-[4,5-Bis-(4-chloro-phenyl)-2-(4-ethoxy-2-methyl-pyrimidin-5-yl)-4,5-dihydro-imidazole-1-carbonyl]-piperazin-1-yl}-1-morpholin-4-yl-ethanone,
cis-4-[2-(2-tert-Butyl-4-ethoxy-pyrimidin-5-yl)-4,5-bis-(4-chloro-phenyl)-4,5-dihydro-imidazole-1-carbonyl]-piperazin-2-one hydrochloride,
cis-2-{4-[2-(2-tert-Butyl-4-ethoxy-pyrimidin-5-yl)-4,5-bis-(4-chloro-phenyl)-4,5-dihydro-imidazole-1-carbonyl]-piperazin-1-yl}-N,N-dimethyl-acetamide hydrochloride, cis-[2-(2-tert-Butyl-4-ethoxy-pyrimidin-5-yl)-4,5-bis-(4-chloro-phenyl)-4,5-dihydro-imidazol-1-yl]-[4-(2-methanesulfonyl-ethyl)-piperazin-1-yl]-methanone hydrochloride, cis-2-{4-[2-(2-tert-Butyl-4-ethoxy-pyrimidin-5-yl)-4,5-bis-(4-chloro-phenyl)-4,5-dihydro-imidazole-1-carbonyl]-piperazin-1-yl}-1-morpholin-4-yl-ethanone, cis-[2-(2-tert-Butyl-4-ethoxy-pyrimidin-5-yl)-4,5-bis-(4-chloro-phenyl)-4,5-dihydro-imidazol-1-yl]-(4-dimethylamino-piperidin-1-yl)-methanone, cis-[2-(2-tert-Butyl-4-ethoxy-pyrimidin-5-yl)-4,5-bis-(4-chloro-phenyl)-4,5-dihydro-imidazol-1-yl]-(4-pyrrolidin-1-yl-piperidin-1-yl)-methanone and cis-1-{4-[2-(2-tert-Butyl-4-ethoxy-pyrimidin-5-yl)-4,5-bis-(4-chloro-phenyl)-4,5-dihydro-imidazole-1-carbonyl]-piperazin-1-yl}-ethanone.

9. A compound of claim 1 selected from the group consisting of cis-[2-(2-tert-Butyl-4-ethoxy-pyrimidin-5-yl)-4,5-bis-(4-chloro-phenyl)-4,5-dihydro-imidazol-1-yl]-(4-methyl-piperazin-1-yl)-methanone, cis-[2-(2-tert-Butyl-4-ethoxy-pyrimidin-5-yl)-4,5-bis-(4-chloro-phenyl)-4,5-dihydro-imidazol-1-yl]-[4-(3-methanesulfonyl-propyl)-piperazin-1-yl]-methanone, cis-[2-(2-tert-Butyl-4-ethoxy-pyrimidin-5-yl)-4,5-bis-(4-chloro-phenyl)-4,5-dihydro-imidazol-1-yl]-[4-(2-hydroxy-ethyl)-piperazin-1-yl]-methanone, 2-{4-[(4S,5R)-2-(2-tert-Butyl-4-ethoxy-pyrimidin-5-yl)-4,5-bis-(4-chloro-phenyl)-4,5-dihydro-imidazole-1-carbonyl]-piperazin-1-yl}-1-morpholin-4-yl-ethanone, 4-[(4S,5R)-2-(2-tert-Butyl-4-ethoxy-pyrimidin-5-yl)-4,5-bis-(4-chloro-phenyl)-4,5-dihydro-imidazole-1-carbonyl]-piperazin-2-one, cis-4-[4,5-Bis-(4-chloro-phenyl)-2-(4,6-diethoxy-pyridin-3-yl)-4,5-dihydro-imidazole-1-carbonyl]-piperazin-2-one hydrochloride, cis-[4,5-Bis-(4-chloro-phenyl)-2-(4,6-diethoxy-pyridin-3-yl)-4,5-dihydro-imidazol-1-yl]-[4-(2-hydroxyethyl)-piperazin-1-yl]-methanone hydrochloride, 2-{4-[(4S,5R)-4,5-Bis-(4-chloro-phenyl)-2-(3-ethoxy-thiophen-2-yl)-4,5-dihydro-imidazole-1-carbonyl]-piperazin-1-yl}-N-tert-butyl-acetamide, 2-{4-[(4S,5R)-4,5-Bis-(4-chloro-phenyl)-2-(3-ethoxy-thiophen-2-yl)-4,5-dihydro-imidazole-1-carbonyl]-piperazin-1-yl}-acetamide, 2-{4-[(4S,5R)-4,5-Bis-(4-chloro-phenyl)-2-(3-ethoxy-thiophen-2-yl)-4,5-dihydro-imidazole-1-carbonyl]-piperazin-1-yl}-N,N-bis-(2-methoxy-ethyl)-acetamide, 2-{4-[(4S,5R)-4,5-Bis-(4-chloro-phenyl)-2-(3-ethoxy-thiophen-2-yl)-4,5-dihydro-imidazole-1-carbonyl]-piperazin-1-yl}-N-methoxy-N-methyl-acetamide, 2-{4-[(4S,5R)-4,5-Bis-(4-chloro-phenyl)-2-(3-ethoxy-thiophen-2-yl)-4,5-dihydro-imidazole-1-carbonyl]-piperazin-1-yl}-N-isopropyl-N-methyl-acetamide, 2-{4-[(4S,5R)-4,5-Bis-(4-chloro-phenyl)-2-(3-ethoxy-thiophen-2-yl)-4,5-dihydro-imidazole-1-carbonyl]-piperazin-1-yl}-N-(2-cyano-ethyl)-N-methyl-acetamide, cis-2-{4-[4,5-Bis-(4-chloro-phenyl)-2-(3-ethoxy-thiophen-2-yl)-4,5-dihydro-imidazole-1-carbonyl]-piperazin-1-yl}-N-(2-methoxy-1-methyl-ethyl)-acetamide and

[(4S,5R)-4,5-Bis-(4-chloro-phenyl)-2-(3-ethoxy-thiophen-2-yl)-4,5-dihydro-imidazol-1-yl]-[4-(3,5-dimethyl-isoxazole-4-carbonyl)-piperazin-1-yl]-methanone.

10. A compound of claim 1 selected from the group consisting of

[(4S,5R)-4,5-Bis-(4-chloro-phenyl)-2-(3-ethoxy-thiophen-2-yl)-4,5-dihydro-imidazol-1-yl]-(4-ethanesulfonyl-piperazin-1-yl)-methanone, N-(2-{4-[(4S,5R)-4,5-Bis-(4-chloro-phenyl)-2-(3-ethoxy-thiophen-2-yl)-4,5-dihydro-imidazole-1-carbonyl]-piperazin-1-yl}-ethyl)-methanesulfonamide,

[(4S,5R)-4,5-Bis-(4-chloro-phenyl)-2-(3-ethoxy-thiophen-2-yl)-4,5-dihydro-imidazol-1-yl]-[4-(3-methanesulfonyl-propyl)-piperazin-1-yl]-methanone,

[(4S,5R)-4,5-Bis-(4-chloro-phenyl)-2-(3-ethoxy-thiophen-2-yl)-4,5-dihydro-imidazol-1-yl]-[4-(2-methanesulfonyl-ethyl)-piperazin-1-yl]-methanone and 2-{4-[(4S,5R)-4,5-Bis-(4-chloro-phenyl)-2-(3-ethoxy-thiophen-2-yl)-4,5-dihydro-imidazole-1-carbonyl]-piperazin-1-yl}-1-morpholin-4-yl-ethanone.

11. A pharmaceutical composition comprising a compound of the formula I

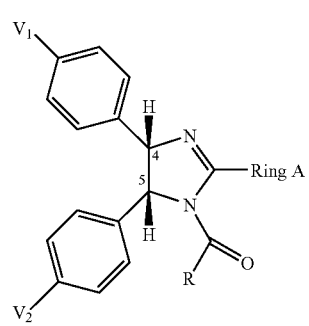

and the pharmaceutically acceptable salts and esters thereof, wherein

Ring A is:

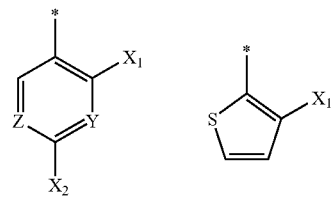

$X_1$ is selected from the group consisting of
   lower alkoxy, and
   lower alkoxy substituted by trifluoromethyl or fluorine;

$X_2$ is selected from the group consisting of
   hydrogen,
   thioalkyl,
   lower alkyl, lower alkoxy,
morpholino, and
—NX₃X₄;
X₃ and X₄ are independently selected from the group consisting of
   hydrogen,
   lower alkyl,
   lower alkyl substituted by lower alkoxy or cyano, and
   lower alkoxy;
Y and Z are independently selected from the group consisting of:
   carbon, and
   nitrogen;
V₁ and V₂ are independently selected from the group consisting of
   halogen,
   cyano, and
   acetylene;

R is selected from the group consisting of
   piperidinyl substituted by five or six membered heterocycle,
   piperidinyl substituted by —NX₃X₄, and

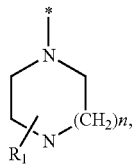

wherein
   n=1 or 2,
R₁ can be one or more substituents selected from the group consisting of
   hydrogen,
   oxo,
   lower alkyl substituted by R₂,
   —C(O)R₃, and
   —SO₂-lower alkyl;
R₂ is selected from the group consisting of
   hydroxy,
   lower alkoxy,
   trifluoromethyl,
   -cyano,
   —NH—SO₂-lower alkyl,
   —NH—C(O)-lower alkyl,
   —C(O)-lower alkyl,
   —C(O)R₄,
   —C(O)—NX₃X₄,
   —SO₂-lower alkyl,
   —SO₂—NX₃X₄,
R₃ is selected from the group consisting of
   five membered heterocycle,
   lower alkyl,
   lower alkoxy, and
   lower alkyl substituted by lower alkoxy and
R₄ is selected from the group consisting of
   hydroxy,
   lower alkoxy,
   morpholino, and
with the proviso that at least one of T and Z is nitrogen
   and a pharmaceutically acceptable carrier.

* * * * *

UNITED STATES PATENT AND TRADEMARK OFFICE
CERTIFICATE OF CORRECTION

PATENT NO. : 7,705,007 B2
APPLICATION NO. : 11/654102
DATED : April 27, 2010
INVENTOR(S) : Nader Fotouhi et al.

It is certified that error appears in the above-identified patent and that said Letters Patent is hereby corrected as shown below:

In Column 46, Claim 11, Line 31 delete
"with the proviso that at least one of T and Z above is nitrogen"

And insert
-- with the proviso that at least one of Y and Z above is nitrogen --

Signed and Sealed this

Twenty-ninth Day of June, 2010

David J. Kappos
*Director of the United States Patent and Trademark Office*